(12) United States Patent
Harrop et al.

(10) Patent No.: US 7,541,044 B2
(45) Date of Patent: Jun. 2, 2009

(54) ADMINISTRATION OF 5T4 ANTIGEN AND IMMUNE RESPONSE OF CELLS EXPRESSING 5T4 AND CEA ANTIGENS

(75) Inventors: Richard Harrop, Oxford (GB); Miles Carroll, Oxford (GB); Susan Kingsman, Oxford (GB)

(73) Assignee: Oxford Biomedica (UK) Limited, Oxford (GB)

( * ) Notice: Subject to any disclaimer, the term of this patent is extended or adjusted under 35 U.S.C. 154(b) by 0 days.

(21) Appl. No.: 11/537,511

(22) Filed: Sep. 29, 2006

(65) Prior Publication Data

US 2007/0086992 A1    Apr. 19, 2007

Related U.S. Application Data

(63) Continuation-in-part of application No. 11/456,530, filed on Jul. 10, 2006, which is a continuation-in-part of application No. PCT/GB2005/000026, filed on Jan. 7, 2005.

(30) Foreign Application Priority Data

Jan. 9, 2004    (GB) ................. 0400443.8

(51) Int. Cl.
*A61K 39/00*    (2006.01)
*A61K 39/12*    (2006.01)
*A61K 39/275*    (2006.01)
*A61K 39/38*    (2006.01)

(52) U.S. Cl. .............. 424/277.1; 424/155.1; 424/184.1; 424/199.1; 424/232.1; 435/344.1; 435/320.1; 435/69.1; 514/2

(58) Field of Classification Search .................. None
See application file for complete search history.

(56) References Cited

U.S. PATENT DOCUMENTS

| | | | |
|---|---|---|---|
| 5,118,672 | A | 6/1992 | Schinazi et al. |
| 5,688,773 | A | 11/1997 | Chiocca et al. |
| 5,869,053 | A | 2/1999 | Stern et al. |
| 5,932,467 | A | 8/1999 | Khan et al. |
| 5,952,225 | A | 9/1999 | Pensiero et al. |
| 6,207,648 | B1 | 3/2001 | Waxman et al. |
| 6,329,199 | B1 | 12/2001 | Pensiero et al. |
| 2002/0102537 | A1 | 8/2002 | Kingsman et al. |

FOREIGN PATENT DOCUMENTS

| | | |
|---|---|---|
| EP | 0110385 A2 | 6/1984 |
| EP | 0198328 A2 | 10/1986 |
| WO | WO89/07947 A1 | 9/1989 |
| WO | WO92/03568 A1 | 3/1992 |
| WO | WO96/04789 A | 2/1996 |
| WO | WO96/30533 A2 | 10/1996 |
| WO | WO97/19183 A1 | 5/1997 |
| WO | WO97/35994 A2 | 10/1997 |
| WO | WO99/15683 A1 | 4/1999 |
| WO | WO99/15684 A2 | 4/1999 |
| WO | WO99/45126 A2 | 9/1999 |
| WO | WO00/17375 A2 | 3/2000 |
| WO | WO 00/29428 * | 5/2000 |
| WO | WO01/66150 A2 | 9/2001 |

OTHER PUBLICATIONS

Bodey, B et al. Anticancer Research [2000] 20:2665-2676.*
Marchand, M et al. Int. J. Cancer [1999] 20:219-230.*
Marchand, M et al. Exp. Opin. Biol. Ther. [2001] 1(3):497-510.*
Harrop et al. (2007) Clinical Cancer Research 13(15): 4487-4494.*
Harrop et al. (2008) Cancer Immunology Immunotherapy 57: 977-986.*
Oxford BioMedica News Release Jul. 31, 2006, No. 2006/OB/15, pp. 1-2.*
Guschlbauer, et al. "Poly-2'-deoxy-2'-fluoro-cytidylic acid: enzymatic synthesis, spectroscopic characterization and interaction with poly-inosinic acid", *Nucleic Acids Res.* (1977) 4:1933.
Schibahara, et al. "Site-directed cleavage of RNA", *Nucleic Acids Res.* (1987) 15:4403.
Gershon, et al. "The nucleotide sequence around the capripoxvirus thymidine kinase gene reveals a gene shared specifically with leporipoxvirus", *J. Gen. Virol*, (1989) 70:525.
Weir, et al. "Nucleotide sequence of the vaccinia virus thymidine kinase gene and the nature of spontaneous frameshift mutations", *J. Virol.* (1983) 46:530.
Esposito, et al. "Nucleotide sequence of the thymidine kinase gene region of monkeypox and variola viruses", *Virology* (1984) 135:561.
Kilpatrick, et al. "Cloning and physical mapping of yada monkey tumor virus DNA" *Virology* (1985) 143:399.
Binns, et al. "Comparison of a conserved region in fowlpox virus and vaccinia virus gnomes and the translocation of the fowlpox virus thymidine kinase gene", *J. Gen Virol* (1988) 69:1275.
Schnitzlein, et al. "A rapid method for identifying the thymidine kinase genes of avipoxviruses", *J. Virological Method* (1988) 23:341.
Fathi, et al. "Efficient targeted insertion of an unselected marker into the vaccinia virus genome", *Virology* (1986) 97:105.
Graham, et al. "A new technique for the assay of infectivity of human adenovirus 5 DNA", *Virol.* (1973) 52:456-467.
Straibinger, et al. "Liposomes as carriers for intracellular delivery of nucleic acids", *Methods in Enzymology*, (1983) 101:512-527.
Studier, et al. "Use of T7 RNA polymerase to direct expression of cloned genes", *Methods in Enzymol.* (1990) 185:60-89.
Matthias, et al. "Eukaryotic expression vectors for the analysis of mutant proteins", *NAR* (1989) 17:6418.
Wootton & Federhen, "Statistics of local complexity in amino acid sequences and sequence databases", *Computers and Chemistry* (1993) 17:149-163.

(Continued)

*Primary Examiner*—Lisa J Hobbs
(74) *Attorney, Agent, or Firm*—Marshall, Gerstein & Borun LLP

(57) ABSTRACT

The invention provides the use of an enzyme and a prodrug in the manufacture of a medicament for use in inducing an anti-tumor immune response in a human patient.

16 Claims, 13 Drawing Sheets

OTHER PUBLICATIONS

Figure 2:
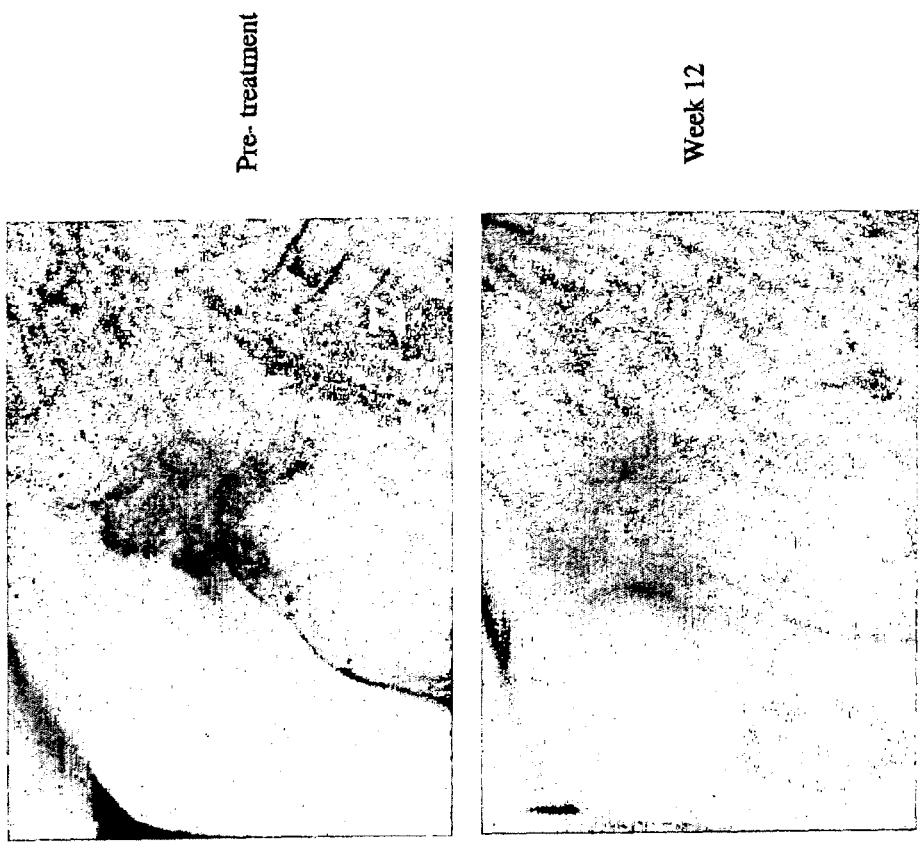

Myers, et al. "Isolation of a cDNA encoding 5T4 oncofetal trophoblast glycoprotein", *J. Biol. Chem.* (1994) 169:9319-9324.

Starzynska, et al. "The expression of 5T4 antigen in colorectal and gastic carcinoma", *Br. J. Cancer* (1992) 66(5):867-869.

Starzynska, et al. "Prognostic significance of 5T4 oncofetal antigen expression in colorectal" *Br. J. Cancer* (1994) 69(5):899-902.

Hobbs, et al. "Polynucleotides containing 2'-amino-2'-deoxyribose and 2'-azido-2'-deoxyribose", *Biochemistry* (1973) 12:5138.

Starzynska, et al. "5T4 oncofetal antigen in gastric carcinoma and its clinical significance", *Eur J. Gastroenterol Hepatol* (1998) 10(6)479-484.

Carsberg, et al. "Metastasis-associated 5T4 antigen disrupts cell-cell contacts and induces cellular motility in epithelial cells", *Int. J. Cancer* (1996) 68(1):84-92.

Yewdell, et al. "TAP-independent delivery of antigenic peptides to the endoplasmic reticulum: therapeutic potential and insights into TAP-dependent antigen processing", *J. Immunotherapy* (1998) 21:127-31.

Calvert, et al. "Fowlpox virus recombinants expressing the envelope glycoprotein of an avian reticuloendotheliosis retrovirus induce neutralizing antibodies and reduce viremia in chickens", *J. of Virol.* (1993) 67:3069-3076.

Carroll, et al. "Construction and characterization of a triple-recombinant vaccinia virus encoding B7-1, interleukin 12, and a model tumor antigen", *J. Natl. Cancer Inst.* (1998) 90(24):1881-1887.

Carroll, et al. "Two bright new faces in gene therapy", *Nature Biotechnology* (1996) 14:556.

Pieken, et al. "Kinetic characterization of ribonuclease-resistant 2'-modified hammerhead ribozymes", *Science* (1991) 253:314-317.

Parker, et al. "Scheme for ranking potential HLA-A2 binding peptides based on independent binding of individual peptide sidechains", *J. Immunol.* (1994) 152:163-175.

Fu, et al. "An endoplasmic reticulum-targeting signal sequence enhances the immunogenicity of an immunorecessive simian virus 40 large T antigen cytotoxic T-lymphocyte epitope", *J. Virol.* (1998) 72:1469-81.

Schodel, et al. "Hepatitis B virus core and e antigen: immune recognition and use as a vaccine carrier moiety", *Intervirology* (1996) 39:104-10.

Wolff and Trubetskoy "The cambrian period of nonviral gene delivery", *Nature Biotechnology* (1998), 16:421-423.

Taylor, et al. "Biological and immunogenic properties of a canarypox-rabies recombinant, ALVAC-RG (vCP65) in non-avian species", *Vaccine* (1995) 13:539-549.

Stannard, et al. "Evidence for incomplete replication of a penquin poxvirus in cells of mammalian origin", *J. Gen. Virol.* (1998) 79:1637-46.

Mackett, et al. "Vaccinia virus: a selectable eukaryotic cloning and expression vector", *PNAS* (1982) 79:7415-7419.

Upton, et al. "Identification and nucleotide sequence of the thymidine kinase gene of shope fibroma virus", *J. Virology* (1986) 60:920.

Boyle, et al. "Fowlpox virus thymidine kinase: nucleotide sequence and relationships to other thymidine kinase", *Virology* (1987) 156:355-365.

Lewis, et al. "Human immunodeficiency virus infection of cells arrested in the cell cycle" *EMBO J.* (1992) 11:3053-3058.

Lewis and Emerman, "Passage through mitosis is required for oncoretroviruses but not for the human immunodeficiency virus", *J. Virol.* (1994) 68:510-516.

Mackett, et al. "General method for production and selection of infectious vaccinia virus recombinants expressing foreign genes", *J. Virol.* (1984) 49:857-864.

Hruby, et al. "Fine structure analysis and nucleotide sequence of the vaccinia virus thymidine kinase gene", *PNAS* (1983) 80:3411-3415.

Lytvyn, et al. "Comparison of the thymidine dinase genes from three entompoxiruses", *J. Gen Virol*, (1992) 73:3235-3240.

Smith, et al. "Vaccinia virus immune evasion", *Immunol Rev.* (1997) 159:137-154.

Jenkins, et al. "Formation of lentivirus particles by mammalian cells infected with recombinant fowlpox virus", *AIDS Research and Human Retroviruses* (1991) 7:991-998.

Taylor, et al. "Recombinant fowlpox virus inducing protective immunity in non-avian species", *Vaccine* (1988) 6:497-503.

Sphener, et al. "Insertion of the fusion gene from Newcastle disease virus into a non-essential region in the terminal repeats of fowlpox virus and demonstration of protective immunity induced by the recombinant", *J. Gen. Virol.* (1990) 71:621-628.

Nakano, et al. "Molecular genetics of vaccinia virus: demonstration of marker rescue", *Proc. Natl. Acad. Sci. USA* (1982) 79:1593-1596.

Chakrabartli, et al. "Vaccinia virus expression vector: coexpression of β-galactosidase provices visual screening of recombinant virus plaques", *Mol. Cell. Biol.* (1985) 3403-3409.

Wigler, et al. "Transformation of mammalian cells with genes from prokaryotes and eukaryotes", *Cell*, (1979) 777-785.

Graessmann, et al. "Microinjection of tissue culture cells", *Meth. Enzymology* (1983) 101:482-492.

Franke, et al. "Neomycin resistance as a dominant selectable marker for selection and isolation of vaccinia virus recombinants", *Mol. Cell. Biol.* (1985) 1918-1924.

Altenburger, W., et al. "Partial deletion of the human host range gene in the attenuated vaccinia virus MVA" *Arch. Virol.* (1989) 105:15-27.

Neumann, et al. "Gene transfer into mouse lyoma cell by electroporation in high electric fields", *EMBO J.* (1982) 1:841-845.

Schaffner, "Direct transfer of cloned genes from bacteria to mammalian cells", *Proc. Natl. Acad. Sci. USA* (1980) 77:2163-2167.

Nestle, F.O., et al. Vaccination of melanoma patients with peptide-or tumor lysate-pulsed dendritic cells, *Nat. Med.* (1998) 4(3):328-32.

Altschul, et al. "Issues in searching molecular sequence database" *Nature Genetics* (1994) 6:119-129.

Carroll, et al. "Host range and cytopathogenicity of the highly attenuated MVA strain of vaccinia virus: propagation and generation of recombinant viruses in a nonhuman mammalian cell line", *Virology* (1997) 238:198-211.

Kim, C. J., et al. "Dendritic cell infected with poxviruses encoding Mart-1/melan a sensitive T lymphocytes in vitro", *J. Immunother* (1997) 20(4):276-86.

Schneider, et al. "Enhanced immunogenicity for CD8 + T cell induction and complete protective efficacy of malaria DNA vaccination by boosting with modified vaccinia virus Ankara", *Nat. Med.* (1998) 4:397-402.

Chakrabarti, et al. "Compact, synthetic, vaccinia virus early/late promoter for protein expression" *Biotechniques* (1997) 23:1094-1097.

Wyatt, et al. "Development of replication-deficient recombinant vaccinia virus vaccine effective against parainfluenza virus 3 infection in an animal model", *Vaccine* (1996) 14:1451-1458.

Sutter, et al. "A recombinant vector derived from the host rangerestricted and highly attenuated MVA strain of vaccinia virus stimulates protective immunity in mice to influenza virus", *Vaccine* (1994) 12:1032-1040.

Carroll, et al. "*E. coli* β-glucuronidase (GUS) as a marker for recombinant vaccinia viruses", *Biotechniques* (1995) 19:352-355.

Hirsch, et al. "Patterns of viral replication correlate with outcome in simian immunodeficiency virus (SIV)- infected macaques: effect of prior immunization with a trivalent SIV vaccine in modified vaccinia virus Ankara", *J. Virol.* (1996) 70:3741-3752.

Sutter, et al. "Nonreplicating vaccinia vector efficiently expresses recombinant genes", *Proc. Natl. Acad. Sci. USA*, (1992) 89:10847-10851.

Bronte, et al. "Antigen expression by dendritic cells correlates with the therapeutic effectiveness of a model recombinant poxvirus tumor vaccine", *Proc. Natl. Acad. Sci. USA* (1997) 94(7):3183-3188.

Wyatt, et al. "Replication-deficient vaccinia virus encoding bacteriophage T7 RNA polymerase for transient gene expression in mammalian cells", *Virology* (1995) 210:202-205.

Carroll, et al. "Highly attenuated modified vaccinia virus Ankara (MVA) as an effective recombinant vector: a Murine tumor model", *Vaccine* (1997) 15:387-394.

Sutter, et al. "Non-replication vaccinia vector efficiently expresses bacteriophage T7 RNA polymerase", *FEBS lett.* (1995) 371:9-12.

Overwijk, et al. "gp100/pmel 17 is a murine tumor rejection antigen induction of Self—reactive, tumoricidal T cells using high-affinity, altered peptide ligand", *J. Exp. Med.* (1998) 188:277-286.

Hole, N., et al. "Isolation and characterization of 5T4, a tumor-associated antigen", *Int. J. Cancer* (1990) 45(1):179-184.

Correale, Pierpaolo, et al. "Generation of Human Cytolytic T Lymphocyte Lines Directed Against Prostate-Specific Antigen (PSA) Employing a PSA Oligoepitope Peptide", *The Journal of Immunology* (1998) 161:3186-3194.

Hodge, James W., et al. "A Recombinant Vaccinia Virus Expressing Human Prostate-Specific Antigen (PSA): Safety and Immunogenicity in a Non-Human Primate", *Int. J. Cancer* (1995) 63:213-237.

Hole, N., et al. "A 72 kD trophoblast glycoprotein defined by a monoclonal antibody", *Br. J. Cancer* (1998) 57:239-246.

Irvine, Kari R., et al. "Synthetic Olignoucleotide Expressed by a Recombinant Vaccinia Virus Elicits Therapeutic CTL", *The Journal of Immunology* (1995) 154:4651-4657.

Jackson, Ronald J., et al. "Infertility in Mice Induced by a Recombinant Ectromelia Virus Expressing Mouse Zona Pellucida Glycoprotein 3", *Biology of Reproduction* (1998) 58:152-159.

Kass, Erik, et al. "Induction of Protective Host Immunity to Carcinoembryonic Antigen (CEA), a Self-Antigen in CEA Transgenic Mice, by Immunizing with a Recombinant Vaccinia-CEA Virus", *Cancer Research* (1999) 59:676-683.

Rosato, Antonio, et al. "CTL Response and Protection Against P815 Tumor Challenge in Mice Immunized with DNA Expressing the Tumor-Specific Antigen P815A", *Human Gene Therapy* (1997) 8:1451-1458.

Sanda, Martin G., et al. "Recombinant Vaccinia-PSA (Prostvac) Can Induce a Prostate-Specific Immune Response in Androgen-Modulated Human Prostate Cancer", *Urology* (1999) 53:260-266.

Southall, P.J., et al. "Immunohistological distribution of 5T4 antigen in normal and malignant tissues", *Br. J. Cancer* (1990) 61:89-95.

Tsang, Kwong Y., et al. "Generation of Human Cytotoxic T Cells Specific for Human Carcinoembryonic Antigen Epitopes From Patients Immunized With Recombinant Vaccinia-CEA Vaccine", *J. Natl. Cancer Inst.* (1995) 87(13):982-990.

Wang, Rong-Fu "Tumor Antigens Discovery: Perspectives for Cancer Therapy", *Molecular Medicine* (1997) 3(11):716-731.

Perkins, David L., et al. "Immunodominance: Intramolecular Competition Between T-Cell Epitopes", *J. Immunol.* (1997) 146(7):2137-2144.

Theobald, Matthias, et al. "The Sequence Alteration Associated with a Mutational Hotspot in p53 Protects Cells from Lysis by Cytotoxic T Lymphocytes Specific for a Flanking Peptide Epitope", *J. Exp. Med.* (1998) 188(6):1017-1028.

Gileadi, Uzi, et al. "Effect of epitope flanking residues on the presentation of N-terminal cytotoxic T lymphocyte epitopes", *Eur. J. Immunol.* (1999) 29:2213-2222.

Engelhard, Victor H. "Structure of peptides associated with MHC class 1 molecules", *Current Opinion in Immunology* (1994) 6:13-23.

Eisenlohr, Laurence C., et al. "Flanking Sequences Influence the Presentation of an Endogenously Synthesized Peptide to Cytotoxic T Lymphocytes", *J. Exp. Med.* (1992) 175:481-487.

Shastri, Nilbah, et al. "Presentation of Endogenous Peptide/MHC Class I Complexes is Profoundly Influenced by Specific C-Terminal Flanking Residues", *J. Immunol.* (1995) 155:4339-4346.

Bergmann, Cornelia C., et al. "Differential Effects of Flanking Residues on Presentation of Epitopes from Chimeric Peptides", *J. Virol.* (1994) 68(8):5306-5310.

Wang, Yusheng, et al. "Silencing of Immunodominant Epitopes by Contiguous Sequences in Complex Synthetic Peptides", *Cell Immunol.* (1992) 143:284-297.

Celis, Esteban, et al. "Identification of Potential CTL Epitopes of Tumor-Associated Antigen Mage-1 for Five Common HLA-A Alleles", *Molec.Immunol.* (1994) 31(18):1423-1430.

Guo, Hwai-Chen, et al. "Different length peptides bind to HLA-Aw68 similarity at their ends but bulge out in the middle", *Nature* (1992) 360:364-366.

Ochoa-Garay, Jorge, et al. "The Ability of Peptides to Induce Cytotoxic T Cells In Vitro Does Not Strongly Correlate With Their Affinity for H-2L$^d$ Molecule: Implications for Vaccine Design and Immunotherapy", *Molec. Immunol.* (1997) 34(3):273-281.

Chaux, Pascal, et al. "Estimation of the Frequencies of Anti-Mage-3 Cytolytic T-Lymphocyte Precursors in Blood From Individuals Without Cancer", *Int. J. Cancer* (1998) 77:538-542.

GenEmbl Accession No. Z29083 (1998).

Stern, Peter, et al. "Characterization of the Human Trophoblast-Leukocyte Antigenic Molecules Defined by a Monoclonal Antibody", *The Journal of Immunology* (1986) 137(5):1604-1609.

Johnson, P.M., et al. Human Trophoblast-Specific Surface Antigens Identified Using Monoclonal Antibodies, *American Journal of Reproductive Immunology* (1981) 1:246-254.

Rettig, Wolfgang J., et al. "Cell Surface Antigens of Human Trophoblast and Choriocarcinoma Defined by Monoclonal Antibodies", *Int. J. Cancer* (1985) 35:469-475.

Hole, M., et al. "Trophoblast-Specific Glycoprotein Defied by Monoclonal Antibody 5T4", *British Society for Immunology & British Transplantation Society 1986 Joint Annual Meeting*. Nov. 12-14, 1986, abstract 66.

Stern, P.L. et al. "Molecular Characterisation of Human Terato-Carcinoma-Trophoblast Cell Surface Antigens", *J. Repro. Immun.*, Supp: 6 (Jun. 1986).

Anderson, Deborah J., et al. Monoclonal antibodies to human trophoblast and sperm antigens: Report of two WHO sponsored workshops, Jun. 30, 1986—Toronto, Canada *J. Repro. Immun.* (1987) 10:231-257.

Cho, S.-W., et al. "Characterization of three monoclonal antibodies to membrane co-factor protein (MCP) of the complement system and quantification of MCP by radioassay", *Clin. Exp. Immunol.* (1991) 83:257-261.

Purcell, D.F.J., et al. "The human cell-surface glycoproteins HuLym5, membrane co-factor protein (MCP) of the complement system, and trophoblast leucocyte-common (TLX) antigen, are CD46", *Immunology* (1990) 70:155-161.

Coulie P. "Human Tumor Antigens Recognized by Cytolytic T Lymphocytes", Chapter 5, pp. 95-125, *Tumor Immunology*, Eds. Dagleish & Browning, Cambridge University Press 1996.

Rosenkrantz, K., et al. "Generation and regulation of autocytotoxicity in mixed lymphocyte cultures: Evidence for active suppression of autocytotoxic cells", *PNAS* (1985) 82:4508-4512.

Stavely-O'Carroll, et al. "Induction of antigen-specific T cell energy: An early event in the course of tumor progression", *PNAS* (1998) 95:1178-1183.

Manson, L, et al. "Short Analytical Review—Anti-tumor Immune Responses of the Tumor Bearing Host: The Case for Antibody-Mediated Immunologic Enhancement", *Clinical Immunology & Immunopathology* (1994) 72(1):1-8.

Ganss, R., et al. "Tumor Microenvironment Can Restrict the Effectiveness of Activated Antitumor Lymphocytes", *Cancer Research* (1998) 58:4673-4681.

Berd, D. "Cancer Vaccines: Reborn or Just Recycled?", *Seminars in Oncology* (1998) 25(6):605-610.

Hersey, P., et al. "Impediments to Successful Immunotherapy", *Pharmcol. Ther.* (1999) 81(2):111-119.

Takahashi, K., et al. "Escape Mechanisms of Melanoma From Immune System By Soluble Melanoma Antigen", *The Journal of Immunology* (1988) 140(9):3244-3248.

Janeway & Travers, *Immunobiology: The Immune System in Health and Disease*, Third edition, Current Biology Ltd./Garland Publishing Inc. (1997).

Amato, R., et al. "Phase II Trial to Assess the Activity of MVA 5T4 (Trovax®) alone versus MVA 5T4 plus Granulocyte Macrophage Colony-Stimulating Factor (GM-CSF) in Patients (pts) with Progressive Hormone Refractory Prostate Cancer (HRPC), Abstract, 18th EORTC-NCI-AACR Symposium on Molecular Targets and Cancer Therapeutics", Nov. 7-10, 2006, Prague, Czech Republic.

Amato, R., et al. "Activity of MVA 5T4 alone or in Combination with either Interleukin-2 (IL-2), Interferon-α (IFN), or Sunitinib in Patients (Pts) with Metastatic Renal Cell Cancer (MRCC), Abstract, 18th EORTC-NCI-AACR Symposium on Molecular Targets and Cancer Therapeutics", Nov. 7-10, 2006, Prague, Czech Republic.

Sykulev, Y., et al. "Evidence that a Single Peptide-MHC Complex on a Target Cell Can Elicit a Cytolytic T Cell Response", *Immunity* (1996) 4:565-571.

Kelly, Patrick F., et al. "RD114-Pseudotyped Oncoretroviral Vectors—Biological and Physical Properties", *Annals New York Academy of Sciences*, (2001) 938:262-277.

Abram, Clare L., et al. "A new retroviral vector, CA1, to identify and select for cells expressing an inserted gene in vitro and in vivo", *Gene* (1997) 196:187-189.

Cosset, Francois-Loic, et al. High-Titer Packaging Cells Producing Recombinant Retroviruses Resistant to Human Serum, *Journal of Virology* (1995) 69(12):7430-7436.

Emi, Nobuhiko. et al. "Pseudotype Formation of Murine Leukemia Virus with the G Protein of Vesicular Stomatitis Virus", *Journal of Virology* (1991) 65(3):1202-1207.

Friedrich, Glenn, et al. "Promoter traps in embryonic stem cells: a genetic screen to identify and mutate developmental genes in mice", *Genes & Dev* (1991) 5:1513-1523.

Kelly, Patrick F., et al. "Highly efficient gene transfer into cord blood nonobese diabetic/severe combined immunodeficiency repopulating cells by oncoretroviral vector particles pseudotyped with the feline endogenous retrovirus (RD114) envelope protein", *Blood* (2000) 96(4):1206-1214.

Kim, V. Narry, et al. "Minimal Requirement for a Lentivirus Vector Based on Human Immunodeficiency Virus Type I" *Journal of Virology*. (1998) 72(1):811-816.

Miletic, Hrvoje, et al. "Retroviral Vectors Pseudotyped with Lymphocytic Choriomeningitis Virus" *Journal of Virology* (1999) 73(7):6114-6116.

Miller A.D , et al. "Improved Retroviral Vectors for Gene Transfer and Expression", *Biotechniques* (1989) 7(9):980-990.

Miller, A.D. "Retroviral Vectors", *Curr Top Microbiol Immunol* (1992) 158:1-24.

Miller, Daniel G. et al. "Gene Transfer by Retrovirus Vectors Occurs Only in Cells That Are Actively Replicating at the Time of Infection", *Molecular and Cellular Biology* (1990) 10:4239-4242.

Miller, Daniel G., et al. "Cloning of the cellular receptor for amphotropic murine retroviruses reveals homology to that for gibbon ape leukemia virus", *PNAS* (1994) 91:78-82.

Miller, Nicholas, et al. "Targeted vectors for gene therapy", *FASEB Journal, Fed. of American Soc. For Experimental Biology*, (1995) 9(2):190-199.

Paillard Florence, "Bystander Effects in Enzyme/Prodrug Gene Therapy", *Human Gene Therapy* (1997) 8:1733-1735.

Patience, Clive, et al. "Packaging of Endogenous Retroviral Sequences in Retroviral Vectors Produced by Murine and Human Packaging Cells", *Journal of Virology* (1998) 72(4):2671-2676.

Rasko, John E., et al. "The RD114/simian type D retrovirus receptor is a neutral amino acid transporter", *Proc. Natl. Acad. Sci.* (1999) 96:2129-2134.

Salmons, Brian., et al. "Construction of Retroviral Vectors For Targeted Delivery and Expression of Therapeutic Genes", *Leukemia* (1995) 9(1):S53-S60.

Soneoka, et al. "A transient three-plasmid expression system for the production of high titer retroviral vectors", *Nucleic Acids Res*.(1995) 23(4):628-633.

Takeuchi, Yasuhiro, et al. "Type C Retrovirus Inactivation by Human Complement Is Determined by both the Viral Genome and the Producer Cell", *Journal of Virology* (1994) 68(12):8001-8007.

Verma, Inder M., et al. "Gene therapy—promises, problems and prospects", *Nature* (1997) 389:239-242.

Yamano, S. et al. "cDNA Cloning and Sequence and cDNA-Directed Expression of Human P450 IIB1: Identification of a Normal and Two Variant cDNAs Derived from the *CYP2B* Locus on Chromosome 19 and Differential Expression of the IIB mRNAs in Human Liver", *Biochemistry* (1989) 28:7340-7348.

Coffin, et al., ed. (1997) *Retroviruses* (Cold Spring Harbor Laboratory Press, Cold Spring Harbor), Table 1, pp. 1-7.

Howard, Bradley D., et al. "Transduction of human pancreatic tumor cells with vesicular stomatitis virus G-pseudotyped retroviral vectors containing a herpes simplex virus thymidine kinase mutant gene enhances bystander effects and sensitivity to glanciclovir", *Cancer Gene Therapy*, (2000) 7(6):927-938.

Zhang, Xian-Yang, et al. "Transduction of Bone-Marrow-Derived Mesenchymal Stem Cells by Using Lentivirus Vectors Pseudotyped with Modified RD114 Envelope Glycoproteins", *Journal of Virology* (2004) 78(3):1219-1229.

Caron, M.C., et al. "A nuclear localization signal in the matrix of spleen necrosis virus 9SNV) does not allow efficient gene transfer into quiescent cells with NSV-derived vectors", *Virology* (2005) 338(2):292-6.

Sandrin, Virginie, et al. "Lentirviral vectors pseudotyped with a modified RD114 envelope glycoprotein show increased stability in sera and augmented transduction of primary lymphocytes and CD34$^+$ cells derived from human and nonhuman primates", *Gene Therapy* (2002) 100(3):823-832.

* cited by examiner

Figure 1
Pt-101
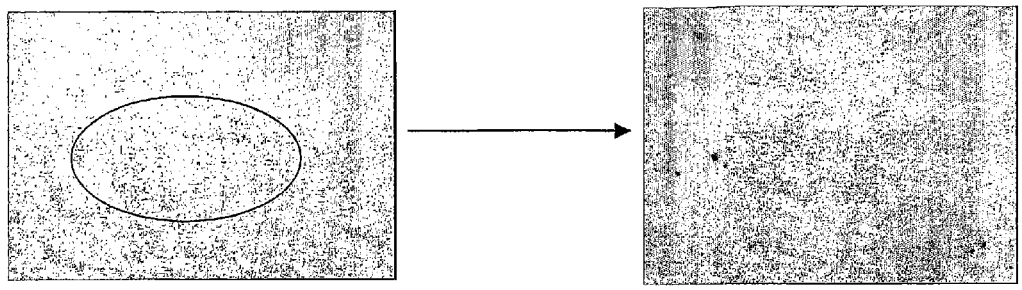
Pt-104
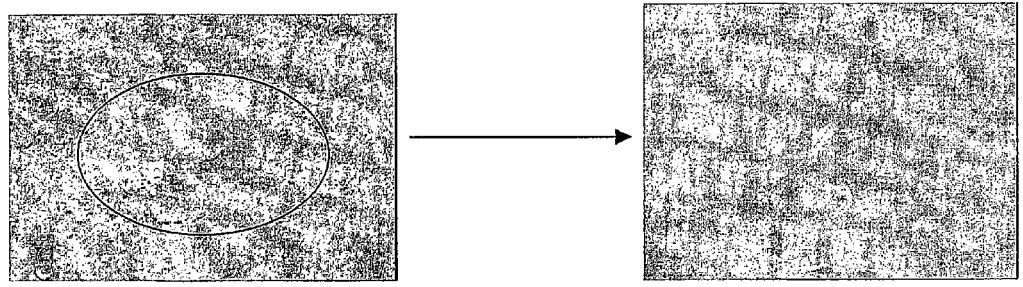
Pt-105
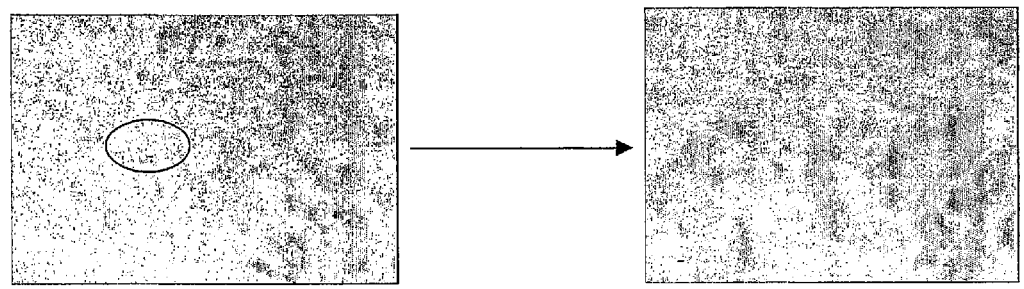
x20 Mag   x40 Mag Figure 2 A-D
A. Pt 101 CEA
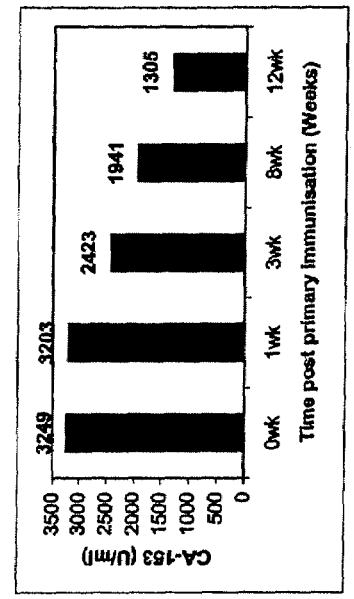
B. Pt 101 CA-153
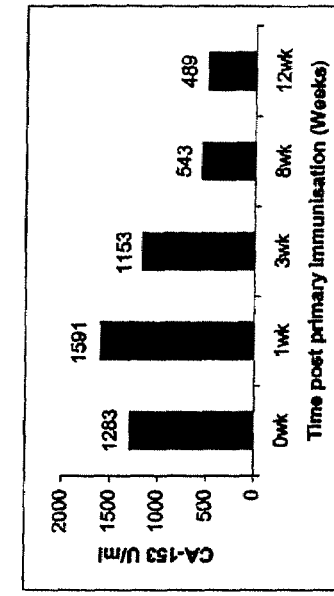
C. Pt 104 CEA
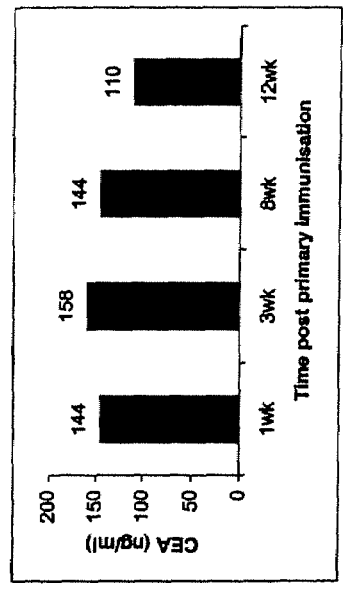
D. Pt 104 CA-153
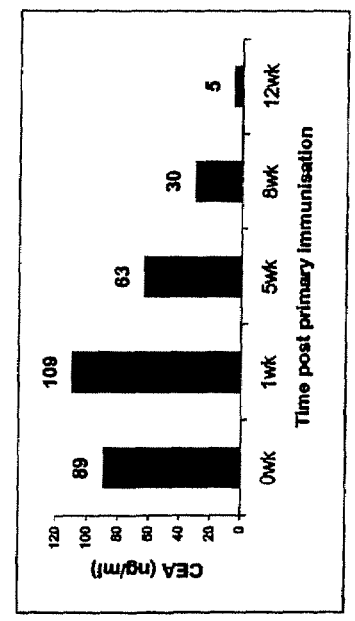

Pt. 104 Clinical Response in Skin Disease

Figure 4
A. Pt 101 Anti-5T4
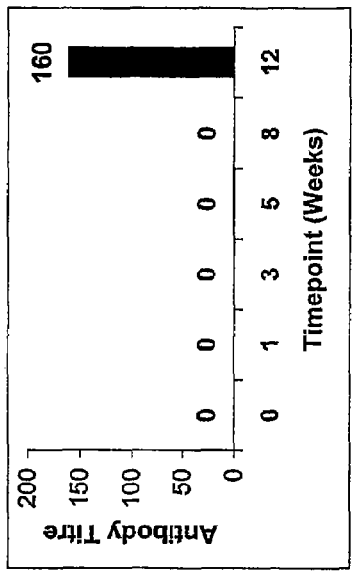
B. Pt 101 Anti-CEA
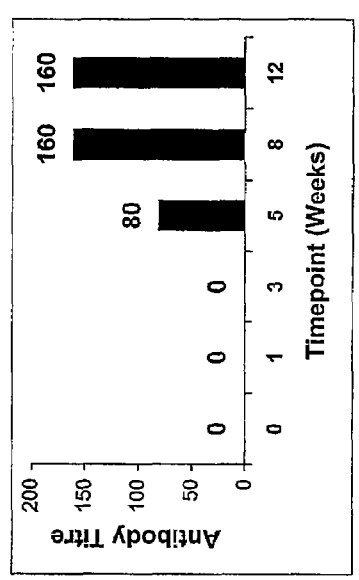
C. Pt 104 Anti-5T4
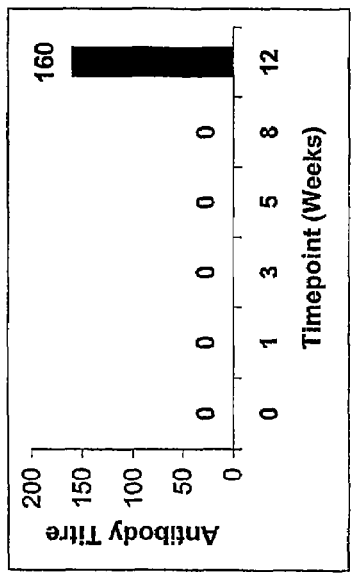
D. Pt 104 Anti-CEA
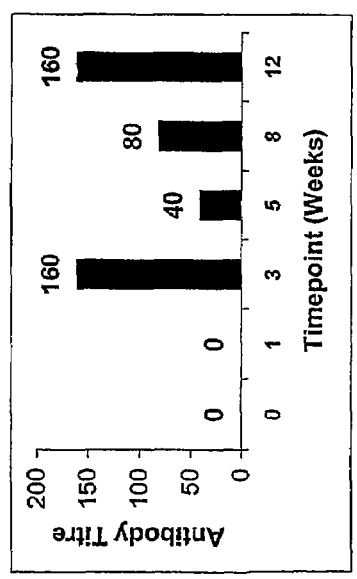

Figure 7:
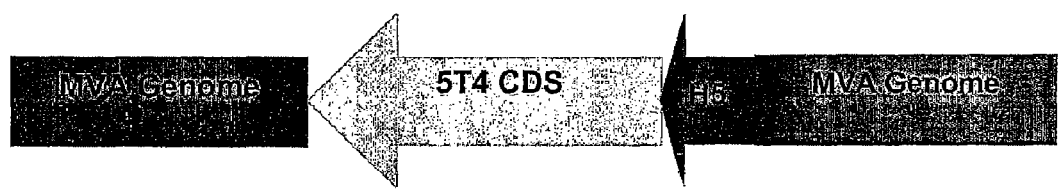

Figure 7: TroVax Construct.

Figure 8: TV-I.M.

Figure 9
A. 5T4 antibody response in patient 102
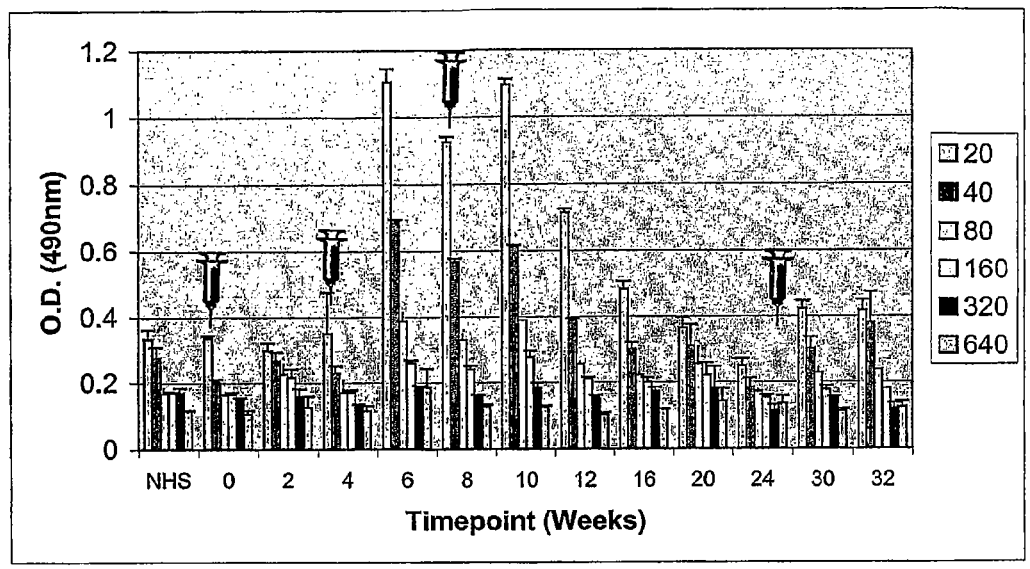
B. CEA antibody response in patient 102
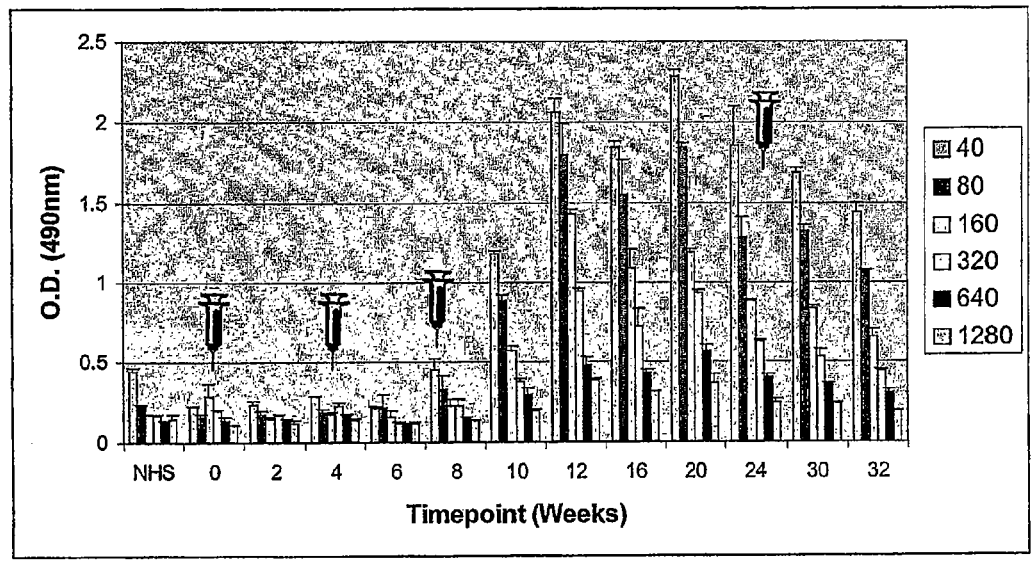

Figure 11:
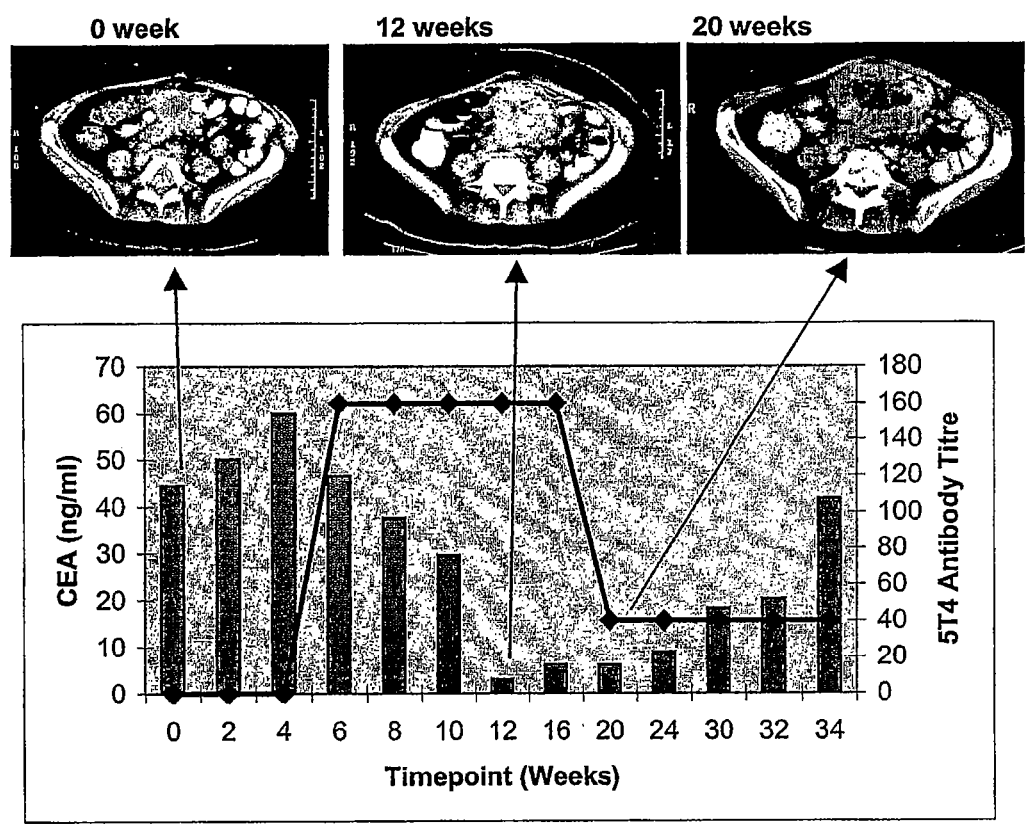

Figure 11: Comparison of circulating levels of plasma CEA (solid bars), 5T4 specific antibody titre (line) and CT scan analysis in patient 102.

ADMINISTRATION OF 5T4 ANTIGEN AND IMMUNE RESPONSE OF CELLS EXPRESSING 5T4 AND CEA ANTIGENS

RELATED APPLICATIONS

This application is a continuation-in-part of U.S. patent application Ser. No. 11/456,530, filed Jul. 10, 2006, which is a continuation-in-part of PCT/GB2005/000026 (published as WO 2005/065718), filed Jan. 7, 2005, which claims benefit of priority to GB 0400443.8, filed Jan. 9, 2004. All three applications are hereby incorporated by reference as if fully set forth.

This application is also related to U.S. patent application Ser. No. 09/533,798, filed Mar. 24, 2000, which claims benefit of priority from U.S. Provisional Patent Applications 60/126,187, filed Mar. 25, 1999, and 60/126,188, filed Mar. 25, 1999, and GB 9825303.2, filed Nov. 18, 1998, GB 9901739.4, filed Jan. 27, 1999, and GB 9917995.4, filed Jul. 30, 1999; and U.S. patent application Ser. No. 10/255,031, filed Sep. 23, 2002, which claims priority to U.S. Provisional Patent Application 60/330,659, filed Oct. 26, 2001, and GB 0122803.0, filed Sep. 21, 2001. All nine of these applications are hereby incorporated by reference as if fully set forth.

FIELD OF THE INVENTION

The present invention relates to methods for stimulating an anti-tumour immune response through the administration of anti-tumour therapy.

BACKGROUND OF THE INVENTION

Administration of cytotoxic chemotherapy is frequently limited by systemic toxicity. Accordingly, a number of strategies for the treatment of tumours in cancer patients have been developed with the aim of improving specificity of cytotoxicity effects such that tumour cells are selectively killed whilst normal, non-tumour, cells are undamaged.

Such strategies include enzyme prodrug therapy and stimulation of cancer cell-specific immune responses.

Enzyme prodrug therapy is a two-step approach: in the first step a drug activating enzyme is targeted and expressed in tumours; in the second step, a non-toxic prodrug which is a substrate of the exogenous drug activating enzyme is administered systemically. The non-toxic prodrug will be converted into the active anticancer drug at high concentration in the local environment of the tumour and thus tumour cells are killed while the systemic drug concentrations are minimised. A number of different enzyme prodrug therapy approaches are reviewed, for example, by Xu and McLeod, Clinical Cancer Research, November 2001, Vol. 7; 3314-3324.

One such approach is exemplified by P450/CYP2B6 expression for the activation of the pro-drug, cyclophosphamide. MetXia-P450 (Oxford Biomedica, Oxford, U.K.) is a novel replication deficient retroviral vector enabling the delivery and subsequent expression of the cytochrome-P450 2B6 gene (CYP2B6) for activation cyclophosphamide within cancer cells (reviewed in Kan, Expert Opin Biol Ther., 2: 857-868, 2002).

After oral or intra-venous administration, cyclophosphamide undergoes metabolism by cytochrome-P450 enzymes (primarily in the liver and to a lesser extent the lung and renal cortex) to 4-hydroxycyclophosphamide and aldophosphamide and then to phosphoramide mustard and acrolein (Colvin, Cancer Treat Rep., 65 Suppl 3: 89-95, 1981; Chang, Cancer Res., 53: 5629-5637, 1993). Phosphoramide mustard is an alkylating agent that induces DNA cross links and strand breaks. Most normal tissues are protected from the activation of cyclophosphamide by the detoxifying effects of aldehyde dehydrogenase (ALDH) and glutathione-S-transferase (GST) that convert aldophosphamide to the inactive carboxyphosphamide. ALDH is frequently absent from cancer cells but may be upregulated in tumours resistant to cyclophosphamide (Hilton, Cancer Res., 44: 5156-5160, 1984; Russo, Cancer Res., 48: 2963-2968, 1988; Russo, Prog Clin Biol Res., 290: 65-79, 1989; Chen, Biochem Pharmacol., 49: 1691-1701, 1995). Experiments in rats demonstrated that stable cell lines transfected with cytochrome P450 2B1 could be made sensitive to cyclophosphamide (Clarke, Cancer Res., 49: 2344-2350, 1989; Chen, Cancer Res., 55: 581-589, 1995). Studies with the human homologue, CYP2B6, confirmed this to be the most efficient P450 isoform for induction of cyclophosphamide mediated cytotoxicity (Chang, 1993; Code, Drug Metab Dispos., 25: 985-993, 1997; Jounaidi, Cancer Res., 58: 4391-4401, 1998). Direct delivery of cytochrome P450 enzymes to tumour cells should increase local activation of cyclophosphamide leading to greater cell kill and less normal tissue toxicity.

Other approaches for stimulating anticancer response have focussed on generating anti-tumour immune responses to human tumours through identifying specific antigens which single out the tumour cells from non-tumour cells such that an immune response is targetted to the unwanted cells. Methods employed include vaccination with a tumour-specific or tumour associated antigen to establish an anti-tumour response. Such methods are reviewed, for example, in Platsoucas et al. AntiCancer Research 23: 1969-1996 (2003).

These different approaches have in common the aim of generating a specific anti-tumour response through specific activation of an enzyme product in a tumour or through eliciting a specific, predetermined anti-tumour immune response to a specific tumour antigen.

However, the most common reason for failure of any anti-tumour therapy is the inability for the response to be maintained and to eliminate any secondary tumours which may develop. Such secondary tumours may differ from the primary tumour in the range of tumour antigens that are expressed or they may be more difficult to target with a construct for expressing a specific enzyme in an enzyme-prodrug approach.

Accordingly, there is a need for a method of treating human tumours that allows a more general response to be elicited against both the primary and secondary tumours.

SUMMARY OF THE INVENTION

The present invention identifies that a general anti-tumour immune response can be stimulated through adminstration of an anti-tumour therapy.

In 1994, there was a report from an animal study that following the introduction of a thymidine kinase (tk) gene and administration of ganciclovir, there was a marked reduction in B16 melanoma lung metastases in immunocompetent but not immunodeficient mice. The investigators suggested that rapid cell death may cause release of tumour antigens and induction of a host immune response against tumour cells (Vile, Int J Cancer, 71: 267-274, 1997; Felzmann, Gene Ther., 4: 1322-1329, 1997) Similar studies were reported in Pierrefite-Carle, 2002 (Pierrefite-Carle et al Gut, 50: 387-391, 2002) using the gene encoding E. coli cytosine deaminase that converts 5-fluorocytosine to 5-fluorouracil. Immune competent rats were injected with a colon carcinoma derived metastatic rat tumour line. After tumours in the liver were established, rats were injected SC with the same tumour line that had been transfected with cytosine deaminase gene before treatment with 5-fluorocytosine. The death of the SC tumour induced an anti-tumour immune bystander effect that caused 70% regression in the volume of the established liver tumours. The anti-tumour effect was shown to be mediated via NK cells. Reports such as these suggested that a TH1 response was induced.

Other reports include Felzmann Gene Ther., 4: 1322-1329, 1997. Here, tumour cells were modified with Adeno HSVtk +/− either Ad IL2, IL6, or B7-1. While the combinations did not improve over that of Adtk/GCV alone (regression in 80% of animals treated), cured animals were protected from further challenge with wild type tumour. However, no protection from challenge with unrelated syngeneic tumours was observed. The anti-tumour immunity correlated with enhanced secretion of GM-CSF from spleen cells of treated animals. IL2, IL6 and IFN γ also increased variably, the latter in the absence of IL4 again suggesting a TH1-mediated response.

A further study reported by Mullen et al. Hum Gene Ther 1998 showed that animals treated with tk-modified tumours +GCV developed specific resistance to re-challenge with unmodified tumour. Again the gene therapy induced tumour necrosis which was associated with cellular infiltrate (CD4+, CD8+ and increased IL12). CTL responses to defined antigens in tk+ cells were greater in GCV-treated groups than those not treated with GCV but harbouring tk+ cells.

However, to this date, the possibility of an anti-tumour response being mounted in response to antigen release from dying tumour cells is not one that has been followed up nor demonstrated to exist in human patients treated with an enzyme prodrug therapy regime. Moreover, none of these studies have suggested that an antibody response directed to a second tumour can be induced.

The present investigators have carried out a clinical trial with MetXia® in late stage breast cancer and melanoma patients (BC1). MetXia® was injected into specific surface tumours of cancer patients. The primary objective of the phase I/II study was to determine the rate of gene transfer to the tumour cells, so a needle biopsy was performed on the injected tumour ~1-2 weeks after injection. Immunohistochemical analysis revealed the presence of β-galactosidase staining due to the integration/expression of the Lac Z gene.

The present investigators have identified that administration of MetXia® in a phase I clinical trial results in the generation of antibodies which are specific for common tumour antigens. In a second trial (BC2) in late-stage cancer patients skin nodules were injected with MetXia®. The objectives of this phase I/II trial included assessment of safety, gene transfer, and immune responses.

Accordingly in a first aspect of the invention, there is provided the use of an enzyme and a prodrug in the manufacture of a medicament for use in stimulating an anti-tumour immune response in a human patient.

In a preferred embodiment the enzyme/prodrug cancer therapy approach is directed against a first tumour in stimulating an anti-tumour immune response against a second tumour in a human patient.

As described above, an "enzyme/prodrug" therapy is a two-step approach comprising targetting expression of an enzyme to tumours and administration of a non-toxic prodrug which is converted to a toxic equivalent. A number of enzyme/prodrug cancer therapy approaches are known to those skilled in the art and reviewed, for example, by Xu and Mcleod, Clinical Cancer Research 2001; Vol. 7; 3314-3324.

In a preferred embodiment, the enzyme/prodrug cancer therapy comprises administering cytochrome p450 in a gene therapy construct followed by administration of an oral oxazaphosphorine drug, for example cyclophosphamide or ifosphamide. Suitable methods are reviewed, for example by Kan, Expert Opin Biol Ther., 2: 857-868, 2002. Suitably administration of cytochrome p450 in a gene therapy construct is administration of MetXia® (Oxford Biomedica, UK).

There are a number of isoforms of cytochrome P450 available in the art, including P450 2B1, P450 2B6, P450 2A6, P450 2C6, P450 2C8, P450 2C9, P450 2C11 and P450 3A4, which may be employed in the present invention. P450 2B6 is preferred. Vectors comprising P450 2B6 have been described in the art; particular reference is made to vectors OB80 and OB83, described in WO03/025191.

Accordingly, there is provided the use of MetXia®-p450 and an oral oxazaphosphorine such as cyclophosphamide or ifosphamide in the manufacture of a medicament for use in stimulating an anti-tumour immune response in a patient.

By "anti-tumour immune response" is meant an immune response characterised by antibodies or by a cellular immune response, including a helper and/or CTL response specific for proteins that are associated with tumours.

Such an anti-tumour response can be detected by identifying the presence of inflammatory cytokines such as, for example, INFγ, IL1, IL6 and IL10, which are indicative of a T-cell response. Alternatively, antibodies can be detected in the patient's blood after administration of the enzyme/prodrug therapy.

Methods for detecting antibodies in a patient sample will be familiar to those skilled in the art. Such suitable methods are described, for example, in "Immunobiology", Janeway and Travers, Current Biology Ltd./Garland publishing and include western blotting techniques, ELISA and so forth.

Previous studies have suggested that a chemotherapeutic approach to the treatment of tumours is associated with an immunosuppressive effect with neutropenia and lymphopenia being common adverse side effects. Nonetheless, a study has shown that a cellular anti-tumour immune response may be observed (see, Nowak et al. Cancer Research 62: 2353-2358, 2002) but, under these conditions, humoral reponses were abolished. This is further demonstrated by, for example, Nowak et al. Cancer Research 63, 4490-4496, 2003, where the induction of a T-helper cell response is observed in the absence of any antibody response.

In contrast, in a preferred aspect of the present invention, the anti-tumour response is an antibody response. A T-cell response is normally required for an antibody response to occur, so the antibody response seen in the present invention occurs together with a T-cell response. Where surface TAAs are concerned, effector functions which are associated with an antibody response are not subject to the influences of HLA downregulation, which impacts strongly on a CTL-mediated effector response. An antibody response can act through other mechanisms, such as an ADCC killing mechanism or a negative feedback mechanism impacting on cell proliferation.

Advantageously, the invention provides a combined antibody and T-cell response.

In particular, the antibody response is an antibody response directed to tumour antigens. Such tumour antigens include CEA and 5T4. Accordingly, in a particularly preferred embodiment, the antibody response is an anti-CEA or an anti-5T4 response.

In a particularly preferred embodiment, the antibody response is one which recognises tumours secondary to the tumour which was the initial target of the enzyme/prodrug therapy. That is, the "first" tumour is that tumour identified or diagnosed and selected as the site for targetted administration of the enzyme for tumour specific expression in an enzyme/prodrug approach whereas the "second" or "secondary" tumours are tumours at a different site or sites. The use of terms such as "second" or "secondary" is non-limiting and does not exclude that further tumours are present in the organism being treated.

In another embodiment, the anti-tumour antibody response stimulated by administration of the enzyme/prodrug therapy can be enhanced by incorporating agents that stimulate an antibody immune response into the gene therapy construct or by coadministration of antibody enhancing agents with the prodrug.

Suitable adjuvants i.e. agents that stimulate an antibody immune response or antibody enhancing agents include, for example, polysaccharides, small molecules and cytokines.

The use of tumour antigens in stimulating a response to a specific anti-tumour antigen, and therefore an anti-tumour immune response, is well documented. However, it has not previously been shown that the induction of an anti-tumour response against a broad range of other non-related tumour antigens can also be stimulated by immunisation against a specific antigen.

Accordingly, in another aspect, the invention provides a use of a first tumour antigen in the manufacture of a medicament for use in stimulating an immune response against a second tumour antigen.

In a preferred embodiment, the first tumour antigen is 5T4. Suitably the 5T4 antigen is provided as an immunogenic composition such as the TroVax® vaccine (Oxford Biomedica, UK).

TroVax® is described in, for example, WO 00/29428, GB 2347932, GB 2370571, GB 2370572 and GB 2378704.

A number of tumour associated antigens (TAAs) are known in the art. TAAs have been characterised either as membrane proteins or altered carbohydrate molecules of glycoproteins and glycolipids, however their functions remain largely unknown. One TAA family, the transmembrane 4 superfamily (TM4SF), usually has four well-conserved membrane-spanning regions, certain cysteine residues and short sequence motifs. There is evidence that TM4SF antigens exist in close association with other important membrane receptors including CD4 and CD8 of T cells (Imai & Yoshie (1993) *J. Immunol.* 151, 6470-6481). It has also been suggested that TM4SF antigens may play a role in signal transduction which in turn, affects cell development, activation and motility. Examples of TM4SF antigens include human melanoma-associated antigen ME491, human and mouse leukocyte surface antigen CD37, and human lymphoblastic leukemia-associated TALLA-1 (Hotta, H. et al. (1988) Cancer Res. 48, 2955-2962; Classon, B. J. et al. (1989) J. Exp. Med. 169: 1497-1502; Tomlinson, M. G. et al. (1996) Mol. Immun. 33: 867-872; Takagi, S. et al. (1995) Int. J. Cancer 61: 706-715).

Further examples of TAAs also include, but are not limited to, TAAs in the following classes: cancer testis antigens (HOM-MEL-40), differentiation antigens (HOM-MEL-55), overexpressed gene products (HOM-MD-21), mutated gene products (NY-COL-2), splice variants (HOM-MD-397), gene amplification products (HOM-NSCLC-11) and cancer related autoantigens (HOM-MEL-2.4) as reviewed in Cancer Vaccines and Immunotherapy (2000) Eds Stem, Beverley and Carroll,, Cambridge University Press, Cambridge. Further examples include, MART-1 (Melanoma Antigen Recognised by T cells-1) MAGE-A (MAGE-A1, MAGE-A2, MAGE-A3, MAGE-A4, MAGE-A6, MAGE-A8, MAGE-A10, MAGE-A12), MAGE B (MAGE-B1-MAGE-B24), MAGE-C (MAGE-C1/CT7, CT10), GAGE (GAGE-1, GAGE-8, PAGE-1, PAGE-4, XAGE-1, XAGE-3), LAGE (LAGE-1a (1S), -1b(1L), NY-ESO-1), SSX (SSX1-SSX-5), BAGE, SCP-1, PRAME (MAPE), SART-1, SART-3, CTp11, TSP50, CT9/BRDT, gp100, MART-1, TRP-1, TRP-2, MELAN-A/MART-1, Carcinoembryonic antigen (CEA), prostate-specific antigen (PSA), MUCIN (MUC-1) and Tyrosinase. TAAs are reviewed in Cancer Immunology (2001) Kluwer Academic Publishers, The Netherlands.

In a preferred embodiment, the immune response against a second tumour antigen is a T-cell or antibody response.

In a particularly preferred embodiment, the second tumour antigen is CEA.

In a further aspect of the invention there is provided a method for inducing an anti-tumour immune response in a subject comprising administering an enzyme/prodrug therapeutic composition to a subject.

In another aspect, there is provided a method for treating a second tumour wherein an enzyme/prodrug approach is directed to a first tumour and wherein said enzyme/prodrug approach induces an immune response against said secondary tumour. Suitably, therefore, said anti-tumour immune response is against a different tumour from the one which is injected with the vector for the enzyme/prodrug approach.

In this context, "treating" a tumour includes arresting or diminishing tumour growth, as well as inducing tumour regression. Moreover, the term includes killing tumour cells, for example resulting in necrosis of the tumour, which may result in a temporary increase in tumour size.

In a further aspect, there is provided a method to treat a subject bearing a tumour comprising administering MetXia®, administering an oxazaphosphorine drug such as cyclophosphamide or ifosfamide and administering an immune stimulatory molecule.

In further aspects, the present invention also relates to methods for monitoring anti-tumour responses induced by tumour therapy.

In one aspect, therefore, there is provided a method of detecting successful treatment with an enzyme/prodrug treatment by measuring presence of anti-tumour antigen antibodies. Suitably, said anti-tumour antigen antibodies include anti-5T4 and anti-CEA antibodies.

In another aspect there is provided a method of identifying and treating cancer patient for treatment comprising the steps of identifying that a tumour in a patient expresses 5T4 or CEA and treating said patient with an enzyme/prodrug therapy.

DETAILED DESCRIPTION OF THE INVENTION

Unless defined otherwise, all technical and scientific terms used herein have the same meaning as commonly understood by one of ordinary skill in the art (e.g., in cell culture, molecular genetics, nucleic acid chemistry, hybridisation techniques and biochemistry). Standard techniques are used for molecular, genetic and biochemical methods. See, generally, Sambrook et al., Molecular Cloning: A Laboratory Manual, 2d ed. (1989) Cold Spring Harbor Laboratory Press, Cold Spring Harbor, N.Y. and Ausubel et al., Short Protocols in Molecular Biology (1999) 4$^{th}$ Ed, John Wiley & Sons, Inc.; as well as Guthrie et al., Guide to Yeast Genetics and Molecular Biology, Methods in Enzymology, Vol. 194, Academic Press, Inc., (1991), PCR Protocols: A Guide to Methods and Applications (Innis, et al. 1990. Academic Press, San Diego, Calif.), McPherson et al., PCR Volume 1, Oxford University Press, (1991), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). These documents are incorporated herein by reference.

Vector Systems

Retroviral vector systems have been proposed as a delivery system for inter alia the transfer of a nucleotide sequence of interest to one or more sites of interest. The transfer can occur in vitro, ex vivo, in vivo, or in combinations thereof. Retroviral vector systems have even been exploited to study various aspects of the retrovirus life cycle, including receptor usage, reverse transcription and RNA packaging (reviewed by Miller, 1992 Curr Top Microbiol Immunol 158:1-24).

As used herein the term "vector system" means a vector particle capable of transducing a recipient cell with a therapeutic gene.

A vector particle includes the following components: a vector genome, which may contain one or more therapeutic genes, a nucleocapsid encapsidating the nucleic acid, and a membrane surrounding the nucleocapsid.

The term "nucleocapsid" refers to at least the group specific viral core proteins (gag) and the viral polymerase (pol) of a retrovirus genome. These proteins encapsidate the packagable sequences and are further surrounded by a membrane containing an envelope glycoprotein.

Once within the cell, the RNA genome from a retroviral vector particle is reverse transcribed into DNA and integrated into the DNA of the recipient cell.

As used herein, the term "vector genome" refers to both to the RNA construct present in the retroviral vector particle and the integrated DNA construct. The term also embraces a separate or isolated DNA construct capable of encoding such an RNA genome. A retroviral genome comprises at least one component part derivable from a retrovirus—such as murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), Moloney murine leukemia virus (Mo-MLV), FBR murine osteosarcoma virus (FBR MSV), Moloney murine sarcoma virus (Mo-MSV), Abelson murine leukemia virus (A-MLV), Avian myelocytomatosis virus-29 (MC29), and Avian erythroblastosis virus (AEV).

MetXia® (Oxford BioMedica) is a retrovirus vector expressing the human cytochrome P450 gene, CYP2B6. MetXia exemplifies an enzyme/prodrug approach for the delivery of a chemotherapeutic agent. TroVax® is a pox virus vector for the delivery of the tumour associated antigen 5T4. Both these viral vectors are based on retroviral vectors. It will be appreciated that other retroviral vectors may be used.

The concept of using viral vectors for gene therapy is well known (Verma and Somia (1997) Nature 389:239-242).

A detailed list of retroviruses may be found in Coffin et al ("Retroviruses" 1997 Cold Spring Harbour Laboratory Press Eds: J M Coffin, S M Hughes, H E Varmus pp 758-763).

The term "derivable" is used in its normal sense as meaning a nucleotide sequence or a part thereof which need not necessarily be obtained from a virus but instead could be derived therefrom. By way of example, the sequence may be prepared synthetically or by use of recombinant DNA techniques.

The viral vector genome is preferably "replication defective" by which we mean that the genome does not comprise sufficient genetic information alone to enable independent replication to produce infectious viral particles within the recipient cell. Preferably, the viral genome lacks a functional env, gag or pol gene. More preferably, the genome lacks env, gag and pol genes.

The viral vector genome comprises some or all of the long terminal repeats (LTRs). Preferably the genome comprises at least part of the LTRs or an analogous sequence which is capable of mediating proviral integration, and transcription. More preferably, the genome comprises a Cytomegalovirus LTR and a MoMLV LTR. Most preferably, the genome comprises a Cytomegalovirus 5' LTR and a MoMLV 3' LTR.

The LTRs may also comprise or act as enhancer-promoter sequences.

The viral vector system of use in the present invention also comprises a therapeutic gene under the control of an internal promoter.

The term "internal promoter" is used herein to indicate a promoter which is distinct from the viral promotor sequences found in the LTRs. Preferably the internal promoter is immediately upstream of the therapeutic gene.

Suitable promoting sequences are preferably strong promoters derived from the genomes of viruses—such as polyoma virus, adenovirus, fowlpox virus, bovine papilloma virus, avian sarcoma virus, cytomegalovirus (CMV), a retrovirus and Simian Virus 40 (SV40)—or from heterologous mammalian promoters—such as the actin promoter or ribosomal protein promoter. Transcription of a gene may be increased further by inserting an enhancer sequence into the vector. Enhancers are relatively orientation and position independent. However, one will typically employ an enhancer from a eukaryotic cell virus—such as the SV40 enhancer on the late side of the replication origin (bp 100-270) and the CMV early promoter enhancer. The enhancer may be spliced into the vector at a position 5' or 3' to the promoter, but is preferably located at a site 5' from the promoter.

In a preferred embodiment, the vectors of use in the present invention may further comprise additional sequences for the expression of immune stimulatory molecules. Such molecules include, for example, GM-CSF (Vaccine. 2002 Jan. 31 ;20(9-10):1466-74. Co-expression of granulocyte-macrophage colony-stimulating factor with antigen enhances humoral and tumor immunity after DNA vaccination. Sun X, Hodge L M, Jones H P, Tabor L, Simecka J W); IL-2 (Mech Ageing Dev. 1997 February;93(1-3):205-14 Effect of rIL-2 treatment on anti-tetanus toxoid response in the elderly. Fagiolo U, Bordin M C, Biselli R, D'Amelio R, Zamarchi R, Amadori A); CpG motifs (Expert Rev Vaccines. 2003 April; 2(2):305-15.CpG DNA as a vaccine adjuvant. Klinman DM); IL-1 (J Immunol. 2001 Jul. 1;167(1):90-7.IL-1 enhances T cell-dependent antibody production through induction of CD40 ligand and OX40 on T cells. Nakae S, Asano M, Horai R, Sakaguchi N, Iwakura Y); CD40L (J Immunol. 1998 Nov. 1;161(9):4563-71.CD40 ligand/trimer DNA enhances both humoral and cellular immune responses and induces protective immunity to infectious and tumor challenge. Gurunathan S, Irvine K R, Wu C Y, Cohen J I, Thomas E, Prussin C, Restifo N P, Seder R A.); IL-15.

Pseudotyping

The vectors of use in the present invention may also be modified in order to engineer particles with different target cell specificities to the native virus, to enable the delivery of genetic material to an expanded or altered range of cell types, or to enhance targetting and uptake to a particular cell type, such as a tumour cell. One manner in which to achieve this is by engineering the virus envelope protein to alter its specificity. Another approach is to introduce a heterologous envelope protein into the vector particle to replace or add to the native envelope protein of the virus.

The term "pseudotyping" means incorporating in at least a part of, or substituting a part of, or replacing all of, an env gene of a viral genome with a heterologous env gene, for example an env gene from another virus. Pseudotyping is not a new phenomenon and examples may be found in WO 99/61639, WO-A-98/05759, WO-A-98/05754, WO-A-97/17457, WO-A-96/09400, WO-A-91/00047 and Mebatsion et al 1997 Cell 90, 841-847.

Pseudotyping can improve retroviral vector stability and transduction efficiency. A pseudotype of murine leukemia virus packaged with lymphocytic choriomeningitis virus (LCMV) has been described (Miletic et al (1999) *J. Virol.* 73:6114-6116) and shown to be stable during ultracentrifugation and capable of infecting several cell lines from different species.

In a particularly preferred embodiment, the vector system of use in the present invention may be pseudotyped with at least part of a heterologous envelope protein or a mutant, variant or homologue thereof. Suitable heterologous envelope proteins may include at least part of the MLV envelope protein or a mutant, variant or homologue thereof which is capable of pseudotyping a variety of different retroviruses. MLV envelope proteins from an amphotropic virus allow transduction of a broad range of cell types including human cells. Another suitable envelope protein may include at least part of the envelope glycoprotein (G) of Vesicular stomatitis virus (VSV) or a mutant, variant or homologue thereof. VSV is a rhabdovirus, which has an envelope protein that has been shown to be capable of pseudotyping certain retroviruses. Its ability to pseudotype MoMLV-based retroviral vectors in the absence of any retroviral envelope proteins was first shown by Emi et al (1991) *Journal of Virology* 65:1202-1207. Another suitable envelope protein may include at least part of the envelope of gibbon ape leukaemia virus (GaLV) or a mutant, variant or homologue thereof.

In a particularly preferred embodiment, the heterologous envelope protein is at least part of RD114 or a mutant, variant or homologue thereof from the RD114/simian type D retroviruses. RD114 is discussed in more detail below.

RD114

The RD114/simian type D retroviruses include the feline endogenous retrovirus RD114, all strains of simian immunosupressive type D retroviruses, the ovian reticuloendotheliosis group including spleen necrosis virus and the baboon endogenous virus. All of these viruses use a common cell surface receptor for cell entry called RD114. The receptor for members of the RD114/type D retrovirus interference group in humans has been identified and cloned (Rasko et al. (1999) *Proc. Natl. Acad. Sci.* 96 2129-2134). A single ORF encoding the receptor is localised within human 19q13.3. The receptor functions as a neutral amino acid transporter and infection of human cells with replication-competent viruses of the RD114/type D retrovirus interference group reduces uptake of neutral amino acids.

It has previously been shown that the use of a retroviral vector system is psuedotyped with the envelope protein of RD 114 enables high levels of gene transfer even when using concentrated stocks of vector. See, for example, WO03/025191.

The sequence of the RD114 env gene is X87829 and is publicly available on the EMBL database.

Pharmaceutical Compositions

The pharmaceutical compositions for use in the present invention comprise a therapeutically effective amount of the retroviral vector system.

Pharmaceutical compositions for human usage will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R. Gennaro edit. 1985). The choice of pharmaceutical carrier, excipient or diluent can be selected with regard to the intended route of administration and standard pharmaceutical practice. The pharmaceutical compositions may comprise as, or in addition to, the carrier, excipient or diluent any suitable binder(s), lubricant(s), suspending agent(s), coating agent(s), solubilising agent(s).

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, pharmaceutical compositions may be formulated to be administered using a mini-pump or by a mucosal route, for example, as a nasal spray or aerosol for inhalation or ingestable solution, or parenterally in which the composition is formulated by an injectable form, for delivery, by, for example, an intravenous, intramuscular, intratumoral or subcutaneous route. Preferably, the pharmaceutical composition of use in the present invention is formulated to be administered parenterally in which the composition is formulated by an injectable form, for delivery, by, for example, an intratumoral route.

Alternatively, the formulation may be designed to be administered by a number of routes.

If the retroviral vector system is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions may be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or the pharmaceutical compositions can be injected parenterally, for example intravenously, intramuscularly or subcutaneously. For parenteral administration, the compositions may be best used in the form of a sterile aqueous solution, which may contain other substances, for example enough salts or monosaccharides to make the solution isotonic with blood. For buccal or sublingual administration the compositions may be administered in the form of tablets or lozenges which can be formulated in a conventional manner.

Administration

A retroviral vector system as a component of an enzyme/prodrug therapy or for the delivery of a tumour associated antigen may be administered alone but will generally be administered as a pharmaceutical composition—e.g. when the components are is in admixture with a suitable pharmaceutical excipient, diluent or carrier selected with regard to the intended route of administration and standard pharmaceutical practice.

If the retroviral vector system encodes a pro-drug activating enzyme then the retroviral vector system will generally be administered in combination with a pro-drug. The retroviral vector system and the pro-drug may be administered at the same time, before or after administration of the retroviral vector system. For example, the pro-drug may be administered one week after the first administration of the retroviral vector system.

For example, the components can be administered in the form of tablets, capsules, ovules, elixirs, solutions or suspensions, which may contain flavouring or colouring agents, for immediate-, delayed-, modified-, sustained-, pulsed- or controlled-release applications.

If the pharmaceutical is a tablet, then the tablet may contain excipients—such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, a cellulose, milk sugar or high molecular weight polyethylene glycols. For aqueous suspensions and/or elixirs, the agent may be combined with various sweetening or flavouring agents, colouring matter or dyes, with emulsifying and/or suspending agents and with diluents such as water, ethanol, propylene glycol and glycerin, and combinations thereof.

The routes for administration (delivery) may include, but are not limited to, one or more of oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intratumoural, intravaginal, intracerebroventricular, intracerebral, subcutaneous, ophthalmic (including intravitreal or intracameral), transferal, rectal, buccal, vaginal, epidural, sublingual or systemic.

For some embodiments, preferably, the route of administration is intratumoral. The injection site may be pre-treated with a local superficial injection of, for example, 2.0% lignocaine. The retroviral vector system described herein may be injected along multiple different tracks within the tumour nodule in order to obtain as wide a dispersion as possible.

Multiple administrations of the vector may give improved gene transfer. There is a rational expectation that this could be true for retroviral vectors because these are limited by the cell cycle status of the target cells. Repeated administrations allow cells in different stages of the cell cycle to be accessed by the vector at different times. Thus, for example, the retroviral vector may be administered in two treatments at each dosage level at a 24 hr interval.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Each patient may be given an injection of an appropriate volume of retroviral vector system relative to the nodule size. For example, a 1 ml dose for use in tumours of 0.5 to 1.5 cm longest dimension; a 2 ml dose for tumours of 1.6 to 2.5 cm longest dimension; a 4 ml dose for tumours of greater than 2.5 cm longest dimension.

The volumes per tumour mass may be based upon an algorithm described by Stopeck et al (1997) *J Clin Oncol* 15, 341 for the administration of DNA based gene therapy. This study suggested the range of 1.0 ml per 0.5 cm to 1.0 cm of dimension with tumours greater than 3 cms receiving 4.0 ml.

For some embodiments, preferably, the maximum dose that will be used is for $5 \times 10^9$ cells per 0.5 cm$^3$. There are approximately $10^9$ cells per cm$^3$ of tissue. Therefore this dose is approximately 10 fold higher than that required to treat all of the cells if the procedure is 100% effective.

Preferably a dose escalation protocol is followed. For example the vector system may be administered by intratumoral injection at escalating doses up to a maximum practical dose of $1 \times 10^9$ lac2 transforming units (Ltu) per 0.5 cm diameter of tumour mass.

Formulation

The component(s) may be formulated into a pharmaceutical composition, such as by mixing with one or more of a suitable carrier, diluent or excipient, by using techniques that are known in the art.

Preferably, the retroviral vector system is administered in an aqueous formulation buffer comprising: Tris, NaCl, lactose, human serum albumin and protamine sulphate. More preferably, the retroviral vector system is administered in an aqueous formulation buffer comprising 19.75 mM Tris, 37.5 mM NaCl, 40 mg/ml lactose, 1 mg/ml human serum albumin and 5 µg/ml protamine sulphate pH 7.0. All the components used are PhEur or equivalent. Protamine sulphate and HSA are purchased as the licensed products Prosulf and Albutein respectively.

The present invention will now be described with reference to the following non-limiting examples and Figures.

FIGURES

FIG. 1: Histological sections showing gene expression.

Representative sections from biopsies taken from 3 patients after intra-tumoural injection of MetXia-P450. Cells are stained with X-gal for the expression of β-galactosidase as described in patients and methods. The presence of blue cells indicates gene expression from *E. coli* lac-Z.

FIG. 2: Measurement of surrogate markers of tumour response

Circulating plasma levels of the surrogate markers CEA (A and C) and CA-153 (B and D) in patients 101 (A and B) and 104 (C and D) are illustrated throughout the 12 week clinical follow up period. Results are expressed as ng CEA per ml plasma or as units (U) CA-153 per ml plasma. (E) clinical response in skin disease.

Figure 3:
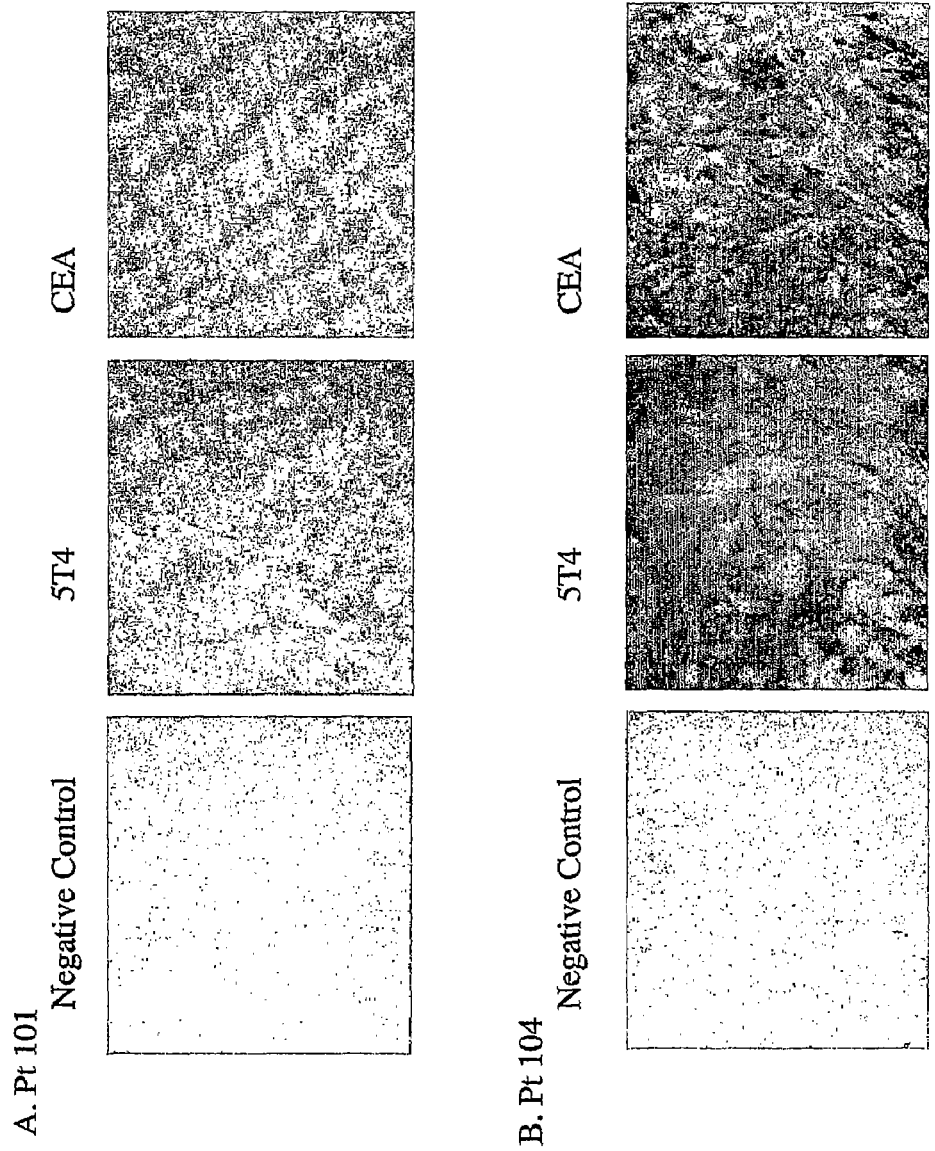

FIG. 3: Tumour antigen profiling of patient biopsies by immunohistochemistry.

The photomicrographs illustrate immunohistochemical staining of tumour biopsies recovered from patients 101 (A) and 104 (B) for expression of h5T4 and CEA.

FIG. 4: Measurement of 5T4 and CEA specific antibody responses

The h5T4 (A and C) and CEA (B and D) specific antibody responses measured in patients 101 (A and B) and 104 (C and D) are shown. Results are illustrated as antibody titre (defined as the greatest serum dilution at which the O.D. is >3× S.D. of the pre-injection (0 wk) sample) throughout the 12 week clinical follow up period.

Figure 5:
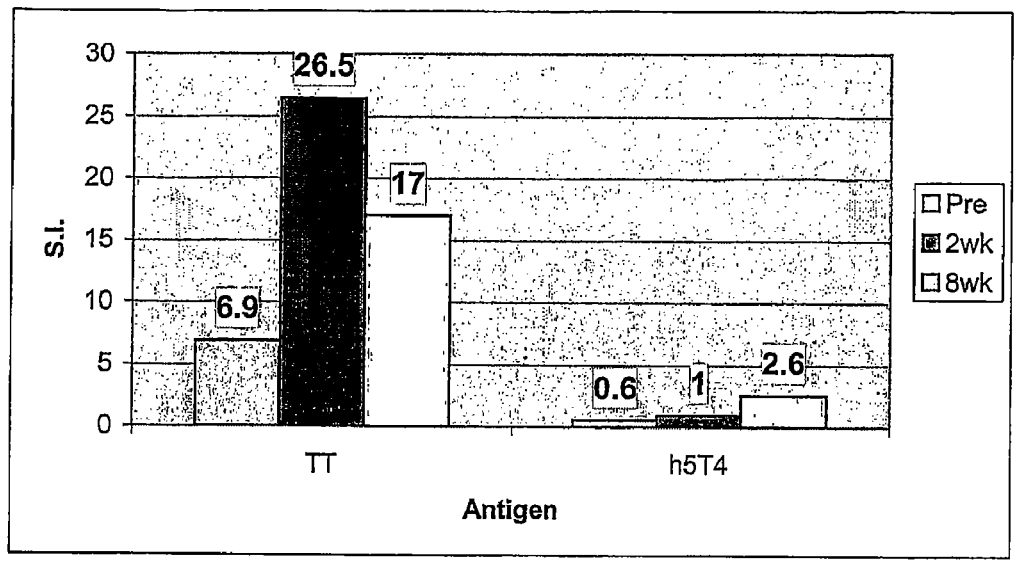

FIG. 5: Proliferative responses of PBMCs from BC1-111 to 5T4 increase post-vaccination.

Figure 6:
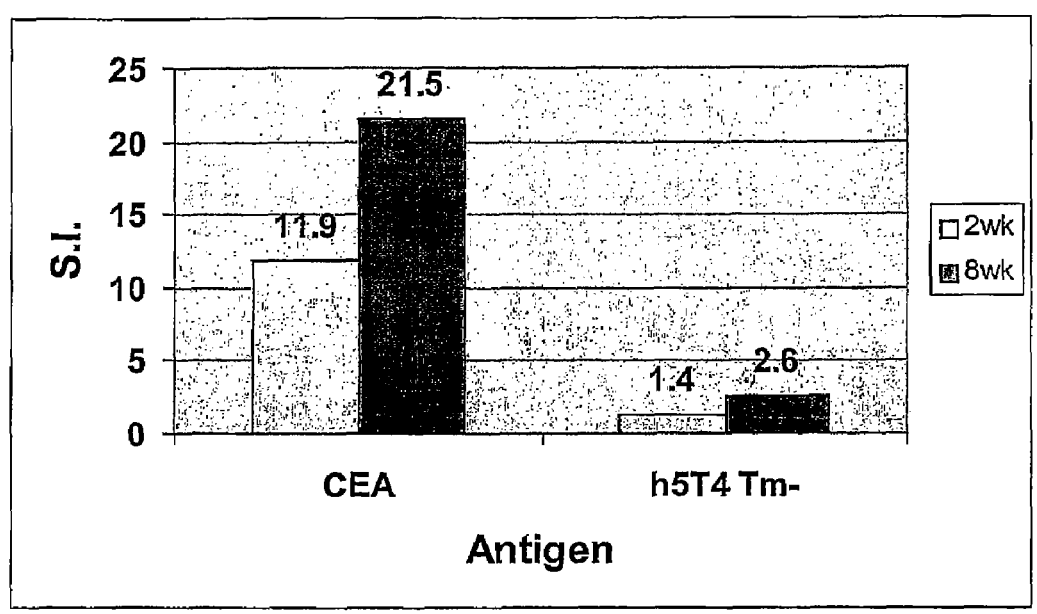

FIG. 6: Proliferative responses of PBMCs from BC1-112 to 5T4 and CEA increase post-vaccination.

FIG. 7: shows a schematic of the TroVax® construct.

Figure 8:
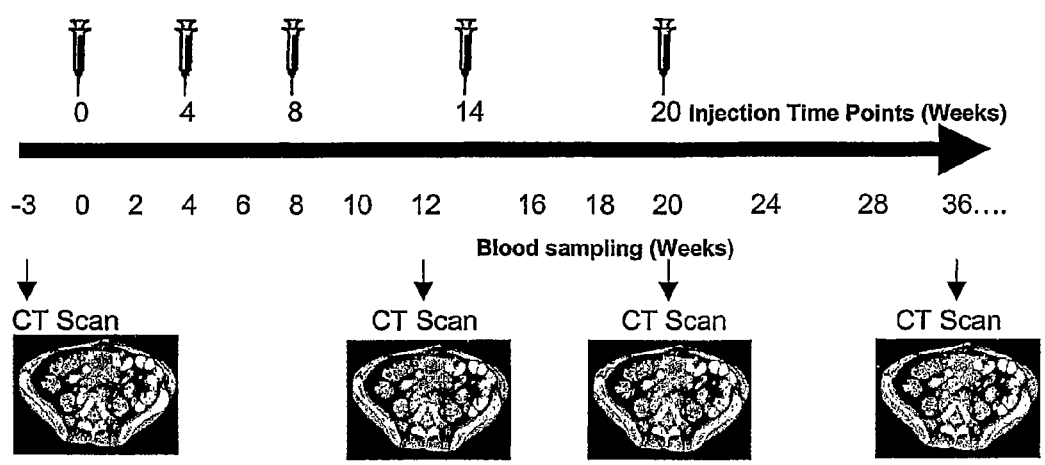

FIG. 8: shows a TV-I.M. Sampling schedule.

FIG. 9: shows a summary of the 5T4(A) and CEA(B) specific antibody responses in patient 102 throughout the vaccination time course.

Figure 10:
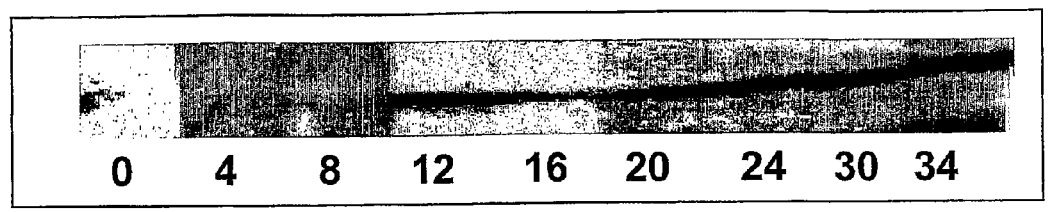

FIG. 10: shows a Western Blot analysis of a purified CEA antigen preparation. Time points are shown in weeks FIG. 11: shows a comparison of circulating levels of plasma CEA (solid bars), 5T4 specific antibody titre (line) and CT scan analysis in patient 102.

Figure 12:
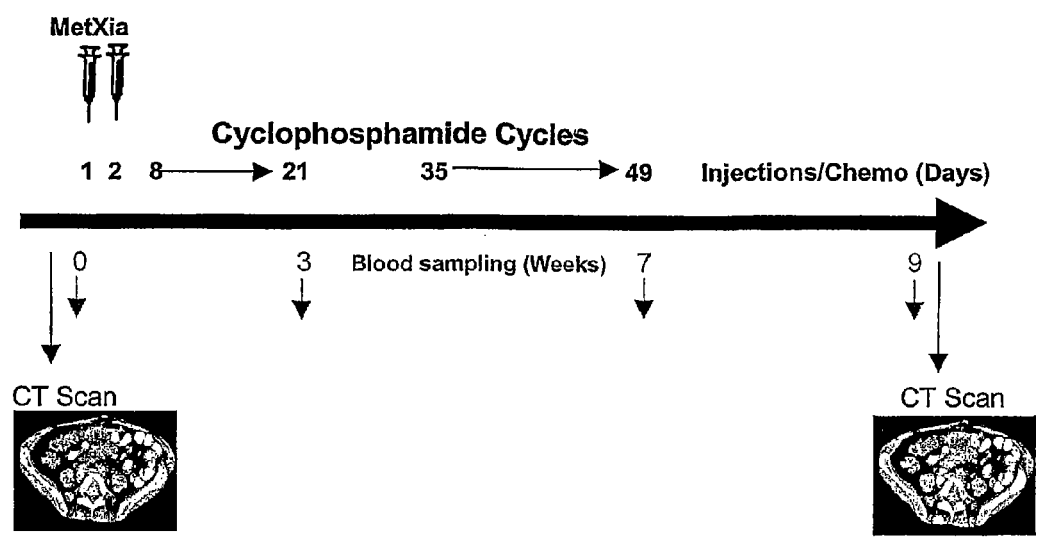

FIG. 12 shows MetXia administration, chemotherapy and immune monitoring schedule for BC2 patients.

EXAMPLES

Introduction

MetXia-P450 is derived from the Moloney murine leukaemia virus (MLV) based retroviral vector. The genome is configured to express CYP2B6 from the MLV long term repeat along with co-ordinate expression of the E. coli lacZ gene enabled by an IRES sequence (reviewed in Kan, Expert Opin Biol Ther., 2: 857-868, 2002). All retroviral sequences, apart from those that are essential for packaging, reverse transcription and integration are removed to prevent replication (Slingsby, Hum Gene Ther., 11: 1439-1451, 2000). The use of a human retro-viral packaging cell line is utilised to extend the vector's biological half-life in human serum and to maximise the concentration of vector (Cosset, J Virol., 69: 7430-7436, 1995).

Kan et al (Kan, Cancer Gene Ther., 8. 473-482, 2001) demonstrated that in vitro, transduction of human HT29 (human colon cancer) and T47D (human breast cancer) cell lines with MetXia-P450 led to sensitisation to cyclophosphamide. These observations were replicated in nude mice in vivo, using HT29, MDA-MB231 (human breast cancer) and MDA-MB468 (human breast cancer) xenografts. MetXia-P450 was directly injected into tumours prior to administration of i.p. cyclophosphamide. Mice treated with both MetXia-P450 and cyclophosphamide had a significant delay in tumour growth compared to those treated with cyclophosphamide alone or an untreated control group. Histological sections found less than 5% of tumour cells expressed lacZ (as an indication of CYP2B6 expression) suggesting a significant bystander effect. Alternatively, MetXia-P450 may induce an anti-tumour antibody response in addition to the direct cytotoxic activation of cyclophosphamide, thereby potentiating its overall potency. The safety of MetXia-P450 was evaluated by intravenous and subcutaneous administration into mice. No adverse reactions were observed during or after administration and no abnormalities were found in any organs at pathological examination of the animals (Kan, Cancer Gene Ther., 8: 473-482, 2001).

The phase I and phase I/II studies were developed to be the first trials of direct intra-tumoural injection of MetXia-P450 in patients with cutaneous tumour deposits from advanced breast cancer or melanoma. Low dose oral cyclophosphamide was subsequently administered to provide an assessment of safety of MetXia in the context of cyclophosphamide as well as to provide the opportunity for efficacy. The primary aims of the study were to determine the safety of the vector and to assess the efficiency of gene transfer. Secondary aims evaluated clinical response and the possibility of induction of an anti-tumour immune response.

Example 1

Phase 1 Study of MetXia-P450 Gene Therapy and Oral Cyclophosphamide for Patients with Advanced Breast Cancer (BC1)

Patients and Methods

MetXia-P450 Production

MetXia-P450 was introduced into a human cell line derived from the FLY-A packaging cell lines as described previously (Slingsby, Hum Gene Ther., 11: 1439-1451, 2000). Briefly, cell lines FLYA13 (derived from human fibrosarcoma cell line HT1080) and TEFLYA (derived from human rhabdomyosarcoma cell line TE671) were transduced and producer clones characterised by β-galactosidase expression and ability to secrete retroviral vector. TEFLYA producer cell clone PTC6 demonstrated greatest transducing power and was used for pre-clinical and clinical testing.

Producer cells were maintained at 80% confluence in growth medium with vector-containing medium collected and replaced by fresh medium every 24 hours. Viral material was isolated by centrifugation and re-suspended in Tris-buffered saline (Tris pH 7.0 19.75 mM, NaCl 37.5 mM, lactose 40 mg/ml, human serum albumin 1 mg/ml, protamine sulphate 5 μg/ml). Average yield was $4 \times 10^7$ to $8 \times 10^7$ lacZ transferring units per ml (Ltu/ml). Formulated clinical product (1 ml) was filled into glass vials at 3 strengths $8 \times 10^5$ Ltu/ml (1×), $8 \times 10^6$ Ltu/ml (10×) or $8 \times 10^7$ Ltu/ml (100×) before freezing at −80° C. Each batch was tested for identity, impurities, adventitious agents, in vitro potency and titre. The product was found to be stable at −80° C. MetXia-P450 for clinical trials was manufactured under contract by Q-One Biotech Ltd. (Glasgow, Scotland).

Patients

Patients with skin nodules from advanced breast cancer or malignant melanoma, not suitable for other systemic treatments, were entered into the study. Inclusion criteria included histological confirmation of cancer with at least one cutaneous tumour nodule $\geq 0.5$ cm in diameter, age $\geq 18$ years, WHO performance status 0-2, expected survival $\geq 3$ months, adequate haematological and biochemical function and no chemotherapy or radiotherapy within 4 weeks (6 weeks for nitrosureas or mitomycin C). Patients with clinical evidence of cerebral metastases or severe intercurrent infection were excluded. The study was approved by the Gene Therapy Advisory Committee and the Central Oxford Research Ethics Committee. All patients gave written informed consent and were treated at the Cancer Research UK Medical Oncology Unit, Oxford.

Administration and Assessment

Prior to treatment eligible patients underwent complete medical history and physical examination, full blood count and biochemical function, staging CT scan, clinical photographs, ECG and, where applicable, pregnancy testing. MetXia-P450 was administered by two intra-tumoural injections 24 hours apart. The vector was thawed for one minute in a 37° C. water bath before direct injection (within 5 minutes) via a 25-gauge needle. Cohorts of patients received either $8 \times 10^5$ Ltu/ml (1×) or $8 \times 10^6$ Ltu/ml (10×) or $8 \times 10^7$ Ltu/ml (100×). Dose escalation was only permitted following safety assessments of patients treated at the preceeding dose level after one course of cyclophosphamide. The volume of MetXia-P450 injected depended upon tumour size (nominally 1 ml for 0.5-1.5 cm, 2 ml for 1.6-2.5 cm and 4 ml for >2.5 cm). All treatment was administered in a side room and, prior to injection, Emla cream (2.5% lidocaine, 2.5% prilocaine) was applied to the tumour nodule for at least one hour. Multiple tracts, via a single entry site, were used for injection to maximise distribution of MetXia-P450 within the tumour. After each treatment the injection site was swabbed and swab tips placed in a sterile container containing 2 ml DMEM before storage at −80° C.. Venous blood was taken into EDTA containing tubes pre-injection and at 1, 4 and 24 hours after the first injection and again at 24 hours after the second injection. Blood was separated into plasma and peripheral blood mononuclear cell (PBMC) fractions by centrifugation before storage at −80° C.

Further assessment was performed in out-patients on day 7. Biopsy of the injected tumour nodules was performed under local anaesthetic. The biopsies were snap-frozen in liquid nitrogen, then sectioned and fixed for histological assessment. Treatment with cyclophosphamide 100 mg/m$^2$ p.o. was commenced for 14 out of every 28 days. Patients were reviewed weekly for the first 8 weeks and end of study assessment, including tumour size and appropriate re-staging CT scans performed at 12 weeks. Response was assessed according to WHO criteria. Patients with stable or responding disease continued with cyclophosphamide at the discretion of the investigator. Toxicity was graded according to NCI-common toxicity criteria (version 2).

Gene Transfer Assessment

Gene transfer was evaluated by histological assessment of frozen biopsy material. Briefly, 5 μm sections were cut using a cryostat and stained for lacZ expression with X-gal. The transduction efficiency and level of therapeutic gene expression was scored according to the number of positively staining cells. Further analysis of gene transfer efficiency was performed using lacZ quantitative PCR (QPCR) from DNA extracted from biopsy material. Data were normalised to the number of cell equivalents sampled with DNA mass determined by GAPDH QPCR.

Immunological Assessment

Humoral Responses

A standard ELISA was used for measurement of both 5T4 and CEA specific antibody titres. Briefly, 96-well plates (Immulon-4, Dynex) were coated overnight at 4° C. in a humid environment with purified antigen (1 μg/ml) diluted in carbonate coating buffer pH 9.6. Wells were then washed briefly with PBS-Tween and incubated with PBS+FBS (10%) for 1 h at room temperature to block non-specific antibody binding. Primary human sera was diluted serially across the plate in PBS-Tween and incubated for 2 hours at room temperature. Wells were then washed 5 times in PBS-Tween and incubated with an anti-human IgG HRP secondary antibody (DAKO; 1:1000) for 2 hours at room temperature. Wells were washed 5 times with PBS-Tween and incubated with an OPD substrate (OPD-Fast; Sigma). The colorimetric change was monitored using a plate reader. All test sera were compared against a pool of sera taken from 10 healthy donors.

Immunohistochemistry

The expression of tumour associated antigens on biopsies taken from each patient was determined by immunohistochemistry. Cryostat sections of biopsied tumours were cut at 5-7 microns using a Leica CM 3050 S cryostat and fixed in acetone. Endogenous peroxidase activity was quenched by incubating slides in 0.2% hydrogen peroxide in methanol for 10 mins. Sections were incubated in 5% normal goat serum in order to block non-specific protein binding sites, before the addition of rabbit anti-CEA antibody (Dako A0115) used at a dilution of 1/300 or mouse anti-H8 (h5T4) antibody (Oxford Biomedica) used at a dilution of 1/1000 and incubated for 1 hour at room temperature. Binding of primary antibodies was detected using Vectorstain elite anti-rabbit ABC (Vector PK-6101) or Vectorstain elite anti-mouse ABC (Vector PK-6102) detection kits as per manufacturers instructions. Slides were washed in 10 mM phosphate buffered saline (PBS) at pH 7.4 containing 0.02% Tween before the application of each reagent. Staining was visualised using 3,3'-diaminobenzidine (Vector DAB substrate kit SK-4100). Sections were counterstained using Mayers haematoxyin and mounted in DPX.

Safety Monitoring

Careful assessments of the safety of MetXia-P450 were undertaken. Skin swabs were taken as described 24 hours after each injection. Thawed samples were plated onto HT 1080 indicator cells and, after incubation, stained with X-gal at 48 hours to test for the presence of infectious vector via expression of lacZ. Batched samples of PBMC's were thawed for RNA extraction and PCR analysis. The presence of free vector in plasma samples was determined by quantitative real time RT-PCR of the lacZ gene. Temporal PCR survey for integrated pro-viral sequences (targeting lacZ sequences) was performed on PBMC's from patients 101-106 whilst the presence or absence of replication competent retroviruses (RCR) was assessed by PCR based assays designed to detect MLV gag-P30 sequences. An increase in signal with time in the samples from an individual patient was used to indicate that an RCR was present.

Further safety assessments evaluated the presence or absence of antibodies against the vector core (gag-P30) or the 4070A envelope protein of the vector. Venous blood samples were taken pre-injection, at 3 weeks and at 12 weeks (or last time point available if patients came off study before 12 weeks). $10^5$ LTU of clinical grade MetXia-P450 vectors, 100 ng of tetanus toxin C fragment (Quadratech) and 10 ng of purified whole human IgG molecules (Chemicon) were loaded individually onto a polyacrylamide gel. After SDS-PAGE, these proteins were transferred onto Hybond ECL membrane (Amersham Biosicences) using a Novex Xcell II mini-cell and blot module (Invitrogen). The membrane was blocked with TBST (Tris-buffered saline pH 7.5 with 1% v/v Tween 20) containing 5% (w/v) fat free dried milk powder. Blocked membrane was then incubated with 50 μl of patient's serum sample followed by an HRP conjugated goat anti-human IgG antibody (Chemicon). The presence of patient's antibodies against the MetXia-P450 vector was visualised by incubation with ECL reagents (Amersham Biosciences) and subsequent exposure to Hyperfilm ECL (Amersham Biosciences). For the detection of antibodies to the vector core, the same membrane was stripped of any residual antibodies and was re-probed with a rat anti-MLV gag-p30 antibody followed by an HRP conjugated goat anti-rat IgG antibody (Dako). The presence of antibodies against vector core were visualised by incubation with ECL reagents and exposure to Hyperfilm ECL.

Results

Patient Characteristics

Twelve patients were enrolled in the study. Demographic data is listed in Table 1. All patients had progressed after standard treatment. Two were treated at 1× dosage, 4 at 10× and 6 at 100×. All patients received two consecutive daily injections of MetXia-P450 into at least one cutaneous nodule and at least one course of cyclophosphamide. Five patients completed the 12 week study period and 7 were withdrawn (2 at 3 weeks, 1 at 4 weeks and 3 at 5 weeks with disease progression. One patient did not attend the 12 week assessment and was considered as non-compliant (from week 8). Four patients continued on treatment with cyclophosphamide on a compassionate basis for 4 (2 patients), 6 and 7 months respectively.

Gene Transfer

Histochemical detection of transduced cells was performed on tumour biopsies at day 7 by staining for X-gal as a marker of β-galactosidase activity. Ten patients (83%) were positive for X-gal staining (Table 2) with only low levels of transduction (<1% of cells) observed (FIG. 1). There was no clear relationship between dose level and β-galactosidase activity although the nature of administration of MetXia-P450 and sampling makes this difficult to assess. A small amount of biopsy material was used for PCR detection of the lacZ gene in the first six patients (2 at 1×, 2 at 10× and 2 at 100×) with positive results observed in 3 patients (one at each dose level, table 2). As a result of the small amount of material used for PCR these results were at the limit of detection for the assay and the negative results were thought to be due to sampling from areas of tumour that had not been close to injection tracts.

Clinical Response

One patient (8%; patient 104) had a partial response. Four patients (33%) had stable disease and the rest (59%) progressive disease. Patient 104 with breast cancer had a partial response documented for 7 months in skin, nodal and hepatic metastases having previously been treated with cytotoxic chemotherapy that included CMF (cyclophosphamide, methotrexate, 5-fluorouracil), MM (mitozantrone, mitomycin C), FEC (5-fluoruracil, epirubicin, cyclophosphamide), docetaxel, capecitabine and vinorelbine. Response was observed at all sites. Interestingly, when her disease subsequently relapsed, she did not have disease progression at the site of the MetXia-P450 injection. Of the patients with stable disease, patient 101 (breast cancer) was noted to have a differential response with a 70% reduction in the size of her injected tumour nodules but no change in the size of her visceral metastases.

Immunological Response

In this study, preliminary analyses were performed to evaluate whether an immune response may have contributed to the observed tumour responses. Serum CEA and CA15-3 were measured in samples from all patients. Elevated pre-treatment levels (>10 ng/ml) of CEA were found in patients 101, 104 and 111 and of CA15-3 (>25 U/ml) in 6 patients (patients 101, 104, 105, 107, 111 and 112). A significant fall in serum CEA was observed in patient 104 and a fall in CA15-3 in patients 101 and 104 (FIG. 2). CA15-3 remained stable for patients 105, 107, 111 and 112 whilst on study. Patient 104 had a documented clinical and radiological partial response and patient 101 stable disease.

For patients who completed at least 8 weeks of the study period tumour biopsy material was stained to detect expression of CEA and h5T4, and antibody titres against CEA and h5T4 were measured in the serum. Strong expression of 5T4 was observed on biopsy material from patients 101, 104, 107 and 111 and of CEA from patients 104, 111 and 112. Representative sections of tumour from patients 101 and 104, stained for CEA and h5T4, are shown in FIG. 3. Interestingly, a significant rise in serum anti-CEA and anti-5T4 antibody titres were observed in patients 101 and 104 by 12 weeks but not in the patients who had no evidence of a clinical or tumour marker response (table 3 and FIG. 4).

Analysis of proliferative responses from BC1 patients 111 and 112 are illustrated in FIGS. 5 and 6. The points are plotted as stimulation index (S.I.) which represent the mean proliferative response of PBMCs assayed in quadruplicate to the test antigen divided by that seen to medium alone. PBMCs were assayed prior to vaccination (Pre) and at 2 and 8 weeks post-vaccination.

Patient 111 (FIG. 5) demonstrated a small increase in the proliferative response induced following in vitro stimulation with 5T4 protein. The response to Tetanus is shown as a control antigen. While the response to tetanus is variable, it is decreasing at week 8 when the response to 5T4 is increasing, suggesting that the response to 5T4 is not due to an elevated level of general immune activity.

Patient 112 showed an increase in proliferative response to both CEA and 5T4 (FIG. 6) at the 8 wk timepoint compared to 2 wk. Although no pre-injection sample was available, the result is suggestive of a role of cytotoxic chemotherapy in the induction of systemic tumour specific immune responses.

Adverse Events

MetXia-P450 was well tolerated with no serious adverse events directly attributable to the investigational agent. Pain (4 patients mild, 1 patient severe), inflammation (1 patient mild) and bleeding (4 patients mild) were observed at the injection site with symptoms resolving in all patients. The main toxicity observed in the study was attributed to oral cyclophosphamide with the most frequent non-haematological events described as nausea (9 patients), alopecia (6 patients), headache (5 patients), anorexia (4 patients) and fatigue (4 patients). All of these events were grade I or II by NCI-CTC with the exception of one patient with grade III fatigue. Two patients had clinically significant haematological toxicity with grade III leucopenia and grade II neutropenia. No patients were admitted with neutropenic fever. There were no consistent biochemical abnormalities attributed to MetXia-P450. During the study 3 patients with breast cancer experienced serious adverse events (patient 103 hypotension, dysarthria and left sided weakness, patient 104 trismus and tongue oedema and patient 108 deep vein thrombosis, hypotension and dyspnoea). None of the serious adverse events were considered related to MetXia-P450.

Safety Assessment

The presence of MetXia-P450 was assessed by skin swabs taken from the injection site, presence of vector in peripheral blood and detection of anti-gag P30 and 4070A envelope antibodies in serum. Low levels of residual vector (approximately 2 Ltu/ml) were detected in swabs from one patient in the 100× group at 24 hours after each injection. Despite this being at the detection limit for the assay, modification to the disinfection method for patients 109 onwards was made with the addition of a further ethanol wipe at the injection site. There was no subsequent detection of viable vector at the skin site. Free vector was only detected by RT-PCR in patients treated with 100× at one hour (4/6, 67%) and four hours (1/6, 17%) with no free vector detected in venous blood from any patient 24 hours after either injection. Antibodies against gag P30 were detected in 3 patients at week 3. One of these patients also had antibodies detected in the pre-treatment serum and 12 week serum. The other two patients were withdrawn from the study with progressive disease before further serum samples were taken. Western blots for the presence of antibodies to vector envelope protein were negative in all patients at each time point evaluated.

Discussion

Conversion of a non-toxic pro-drug, to an active metabolite, within a cancer cell provides a potential technique for delivery of high local concentrations of cytotoxic chemotherapy to the target tumour. In this phase one study, MetXia-P450 was directly injected into at least one cutaneous tumour deposit on 2 consecutive days with biopsy of the nodule a week later. Low dose oral cyclophosphamide was subsequently administered. Direct injection was chosen to maximise local delivery to the tumour. Previous experiments had demonstrated that this technique did not impact on vector viability and could be used to transduce mouse xenograft models (Kan, Cancer Gene Ther., 8: 473-482, 2001). In this trial, expression of β galactosidase as a surrogate indicator for CYP2B6, found that gene transfer was achieved in most (10/12) patients. However, histological staining with X-gal showed only low levels of transduction with less than 1% of cells expressing lacZ. PCR techniques, in three out of six biopsies assessed, confirmed this low but consistent level of lacZ expression. The reason that PCR appeared less sensitive is due to the level of expression being at the limit of detection of the assay for the small amount of biopsy material used. There was no evidence of increased transduction efficiency with higher dose levels although the minimally invasive biopsy procedure was not likely to yield this level of qualitative analysis.

Efficient gene transfer has been one of the main limiting factors in gene therapy development. Retroviral transduction of cancer cells is a multi-step process dependent upon diffusion and absorption of viral particles onto the cell surface, binding of the viral envelope to the plasma membrane, absorption into the cell nucleus and integration of a DNA copy of the retroviral genes into the cancer cell genome. Failure of any one step in the process will prevent transduction and viral gene expression. Despite direct injection, the technique of administration is limited by the distribution of the vector along the needle tracts with incomplete coverage of the whole tumour nodule. The low levels of expression of P galactosidase observed in this trial are comparable to those observed in a recently published study utilising adenovirus mediated gene therapy directly injected into recurrent gliomas via an implantable catheter. Resection material from that trial only found transfected cells on average within 5 mm of the injection site (Lang et al., J Clin Oncol., 21: 2508-2518, 2003). Whilst a low level of transduction is disappointing, even small increases in metabolism of cyclophosphamide could lead to a significant increase in tumour cell kill because of diffusion of the metabolites to neighbouring cells leading to a bystander effect (Wei, Clin Cancer Res., 1: 1171-1177, 1995; Chen, Biochem Pharmacol., 49: 1691-1701, 1995). Indeed, in mouse xenografts, a significant reduction in tumour growth rates were seen with MetXia-P450 plus cyclophosphamide when compared to cyclophosphamide alone, with a transduction efficiency of less than 5% (Kan, Cancer Gene Ther., 8: 473-482, 2001). However, the relative contribution of MetXia-P450 CYP2B6 metabolism of cyclophosphamide, as compared with hepatic metabolism, is not known for patients treated in this clinical trial.

Whilst primarily evaluating the efficacy of gene transfer this study also looked at clinical and immunological responses to MetXia-P450 in combination with low dose oral cyclophosphamide. Tumour markers CA15-3 and CEA were measured to provide surrogate indicators of response whilst tumour expression of, and antibodies against, CEA and h5T4 were studied for evidence of immunological activation. 5T4 is an oncofetal antigen that is expressed in low levels in normal tissue epithelia but is frequently over-expressed in tumour cells including colon, gastric and breast cancers. Over-expression has been associated with a worse prognosis in gastric tumours (Southall et al., Br J Cancer, 61: 89-95, 1990; Mulder et al., Clin Cancer Res., 3: 1923-1930, 1997; Woods et al., Biochem J., 366: 353-365, 2002). In the current trial one heavily pre-treated patient with breast cancer (patient 104) had a documented and persisting partial response both at the injected lesion and at distant sites (FIG. 4c). Her previous treatment had included two schedules of chemotherapy that contained intra-venous cyclophosphamide. Another patient had evidence of tumour response at the site of the injected lesion only. In both these patients there was a fall in serum CEA associated with a rise in anti-CEA and anti-5T4 antibody titres during the 12 week study period. The responses are most likely to be due to the cytotoxic activity of low dose cyclophosphamide alone although the expectation of significant tumour responses in this clinical setting are low. However, alternative mechanisms of action are possible. The presence of antibody induction in one patient with a documented clinical response and in another with stable disease associated with a significant fall in serum CA15-3 suggests an anti-tumour immune effect. This may be due to the actions of cyclophosphamide alone but may also be attributed to the potential increased tumour cell kill and release of tumour associated antigens at the site of MetXia-P450 injection. This phenomena of anti-tumour immune bystander effects, following gene-directed enzyme prodrug therapy, has previously only been reported in animal studies (Vile, Cancer Res., 54: 6228-6234, 1994; Vile, Int J Cancer, 71: 267-274, 1997; Pierrefite-Carle, Gut, 50: 387-391, 2002).

An important end-point of this study was to determine the safety and toxicity of MetXia-P450. Extensive monitoring was performed for the presence of viable vector at the injection sites as well as any systemic effects. Swabs from the injection site showed the presence of viable vector in one patient at 24 hours. For all subsequent patients the procedure to disinfect the skin was modified to include a second ethanol wipe of the injection site. No viable virus was detected at the injection sites in the patients treated after this modification. The presence of vector in the plasma of patients treated was assessed by real time PCR. Free vector could be detected in four out of six patients at the 100× level one hour after injection and in one of these patients at 4 hours. No free vector was detected in any patients 24 hours after injection. Anti-gag P30 antibodies were detected in 3 patients 3 weeks after injection (one of these patients had pre-treatment antibodies that persisted at 12 weeks). These assessments suggest that low levels of MetXia-P450 reach the systemic circulation in patients treated by intra-tumoural injection at the 100× strength, with a small proportion of patients developing an immune response. Direct toxicity from MetXia-P450 was minimal. A small number of patients reported pain, bleeding or inflammation at the injection site but, in all cases, this had resolved within 48 hours. No systemic toxicity or serious adverse events were associated with MetXia-P450. The only toxicities observed were all attributed to oral cyclophosphamide with two patients experiencing significant neutropenia. Non-haematological toxicity was mild with nausea, alopecia, headaches, fatigue and anorexia reported.

In conclusion, this phase one study has demonstrated that intra-tumoural injection of MetXia-P450 is safe and well tolerated. Low, but consistent levels of gene transfer were observed at all dose levels suggesting that expression of CYP2B6 from MetXia-P450 can be achieved within tumour cells.

Example 2

TroVax®

Patients

All patients enrolled into the trial had Duke's D colorectal cancer, a WHO performance status of 0,1 or 2 and were expected to live for >3 months. Patients were assigned randomly to 3 groups commencing at the lowest dose. Group one received $5 \times 10^7$ pfu (1×), group 2 $1 \times 10^8$ pfu (5×) and group 3 $5 \times 10^8$ pfu (10×) of TroVax.

A schematic for the TroVax construct used is given in FIG. 7. 5T4 was inserted into deletion region III of MVA by homologous recombination and placed under the control of the early/late vaccinia modified H5 promoter.

Vaccination and Monitoring Regimen

Injections were performed at 0, 4 and 8 weeks. If patients mounted an immunological or clinical response, a further 2 injections were offered at weeks 14 and 20. All patients provided blood samples every 2 weeks for the first 3 months and at approximately monthly intervals thereafter for the subsequent 6 months (FIG. 8). CT scans were performed at the −3 wk injection timepoint and at 12, 20 and 36 weeks post-injection.

TV-1 Sampling Schedule

The schematic shown in FIG. 8 illustrates each vaccination timepoint (syringe) and, below the solid arrow, timepoints at which blood samples were taken and CT scans performed.

Throughout the vaccination timecourse, immune responses to a number of proteins were monitored, including the tumour associated antigens 5T4 and CEA. FIG. 9 (A and B) illustrates the 5T4 (A) and CEA (B) specific antibody responses induced following vaccination with TroVax in patient 102. Syringes indicate the timing of each injection (weeks 0, 4, 8, and 28). Results are expressed as the mean O.D.±S.D. for each serum dilution tested (1:20 to 1:640 for 5T4 and 1:40 to 1:1280 for CEA responses).

The specificity of the CEA antibody response was determined by Western blot analysis. FIG. 10 shows a Western blot a purified CEA antigen preparation electro-blotted onto nitro-cellulose and probed with patient 102 sera at different timepoints throughout the vaccination timecourse.

Serum taken from patient 102 prior to week 12 does not detect the purified CEA protein immobilised on the blot. However, from week 12 to 34, CEA is detected strongly by the serum. This corresponds to the pattern of CEA specific antibody levels measured by ELISA (FIG. 9B) as described earlier in this document.

Results

A strong CEA specific antibody response is detected in TV1 patient 102, but this occurs approximately 4 weeks after the induction of a 5T4 specific antibody response. Measurement of the surrogate disease marker CEA (FIG. 9) in patient 102 showed a significant decline from weeks 6-12. This decline in circulating CEA was coincident with the presence of both 5T4 and CEA specific antibody and cellular responses and evidence of tumour necrosis.

Example 3

MetXia Phase I/II Clinical Trial (BC2)

1. Patient Details

A total of eight patients were recruited to the BC2 trial, 4 patients at a 10× and 4 at a 100× dose. Patient details are listed in Table 4.

2. Immune Monitoring of BC2 Patients

The sampling schedule for BC2 patients is shown schematically in FIG. 12. All patients enrolled in the trial provided blood samples for immunomonitoring at 0, 3, 7 and 9 weeks following trial initiation. Two injections of MetXia were given on day 1 and 2 and two cycles of cyclophosphamide were administered between days 8 and 21 and 35 and 49.

FIG. 12 shows MetXia administration, chemotherapy and immune monitoring schedule for BC2 patients. In addition to the sampling detailed in FIG. 12, a biopsy is taken at day 7 for analysis of gene transfer and tumour antigen profiling.

It should be emphasised that all immune monitoring is performed on peripheral blood samples and as such, may only provide an indication of events occurring at the tumour site. At each sampling timepoint, immune responses were monitored as follows:

i. Cellular Responses

Proliferation assay: Measurement of proliferative responses of human lymphocytes is a fundamental technique for the assessment of reactivity to various antigenic stimuli. Incorporation of a radiolabel ($^3$H-Thymidine) into cellular DNA is a common method to assess a proliferative T-cell response to antigen. This assay continues to be used extensively, because clonal expansion of a TAA-specific T cell population is the desired outcome of any vaccination protocol. The assay is usually used as a surrogate for a Class II (CD4) restricted response as the incubation of antigen-presenting cells with soluble antigen requires protein uptake, and most likely, preferential processing of that antigen in the class II pathway. Results from proliferation assays are often reported as a stimulation index which is defined as:

$$S.I. = \frac{\text{Incorporation of } ^3H\text{-Thymidine by PBMCs cultured with test antigen}}{\text{Incorporation of } ^3H\text{-Thymidine by PBMCs cultured with medium alone}}$$

An SI≧2 is considered to be a positive result. An increase in SI to a specific antigen following immunisation is indicative of a positive immune response induced by the vaccine. All proliferation assays were performed Current Protocols in Immunology. Eds John E Coligan et al, Section II Unit 7. 10.

ii. Antibody Responses.

ELISA: The analysis of antigen-specific antibody responses by ELISA is a widely utilised and well-established technique. The assay provides a relative measure of antigen-specific antibody concentration in the serum and can be used to determine if vaccination increases the concentration of the antibody of interest. All ELISA assays were performed as described above.

3. Results 3.1 Cellular Proliferative Responses

Proliferative responses were measured at every sampling timepoint for each patient. The primary goal was to monitor the responses to tumour associated antigens e.g. 5T4 and CEA proteins. In addition to the purified 5T4 protein, a peptide library was also available (overlapping 20 mer 5T4 peptides) for analysis of proliferative responses. Tables 5a-c provide a summary of all the proliferative responses measured in each patient.

Tables 5 a, b and c: Summary proliferative responses of patient PBMCs following in vitro restimulation with (a) 5T4 protein, (b) 5T4 peptides or (c) CEA. Results are expressed as a stimulation index (proliferation induced by test antigen÷proliferation induced by medium alone). A stimulation index ≧2 is considered to be positive (highlighted). Results from patients who showed a greater than 2 fold increase post-MetXia are tabulated in bold text. "n/a" indicates patients who were withdrawn before completion of the 9 week monitoring period.

Five patients (BC2-101, BC2-102, BC2-104, BC2-203 and BC2-204) showed positive proliferative responses to 5T4 protein (Table 5a) which were not evident prior to administration of MetXia. Two patients (BC2-201 and BC2-202) showed pre-existing proliferative responses which did not increase significantly after MetXia injection. Four patients (BC2-101, BC2-102, BC2-103 and BC2-104) showed positive proliferative responses to 5T4 peptides (Table 5b) which were not evident prior to administration of MetXia. Three patients (BC2-201, BC2-202 and BC2-203) showed pre-existing proliferative responses to some 5T4 peptides which did not increase following MetXia administration. Six patients showed pre-existing CEA proliferative responses (Table 5c), two of which (BC2-102 and BC2-104) showed a significant increase following MetXia administration. One patient (BC2-202) showed no pre-existing response prior to treatment, but was positive at week 9.

2.2 Immunohistochemistry

All BC2 biopsies taken 1 week post-immunisation were stained for a panel of tumour antigens including Muc-1, Her-2, Survivin, CEA and 5T4 (Table 6).

2.4 Analysis of Biopsies for Gene Transfer and Tumour Antigen Profiling

Overall Summary

A summary of all immunological monitoring data obtained from all 8 BC2 patients at each sampling timepoint is given in Table 7.

Table 7: Summary of immunological responses in BC2 patients. The table summarises the proliferative responses specific for 5T4 and CEA mounted by BC2 patients throughout the 9 week monitoring period and also the tumour antigen status of the tumour biopsies assessed by immunohistochemistry. Results are simply tabulated as yes or no, where yes indicates that an immunological response has been induced, or increased significantly, following MetXia administration.

- Six patients (BC2-101, BC2-102, BC2-104, BC2-202, BC2-203 and BC2-204) completed the 9 week monitoring period. Two patients (BC2-103 and BC2-201) withdrew at week 3.
- Seven patients showed either de novo or significantly enhanced ($\geq 2$ fold) immunological responses to 5T4 or CEA following administration of MetXia.
- Patients BC2-102, BC2-104 and BC2-202 showed an increased proliferative response to CEA following administration of MetXia and CPA treatment.
- Patients BC2-101, BC2-102, BC2-104, BC2-203 and BC2-204 showed positive proliferative responses to 5T4 protein following, but not prior to, administration of MetXia.
- Biopsies removed from all BC2 patients showed 3 (BC2-101, BC2-102 and BC2-204) to be positive for 5T4 expression and 7 to be positive for CEA.

TABLE 1

Patient characteristics (BC1)

| | |
|---|---|
| Number of patients | 12 |
| Female | 10 |
| Male | 2 |
| Tumour type | |
| Breast | 9 |
| Melanoma | 3 |
| Median age (range), years | 59 (34-74) |
| ECOG performance status | |
| 0 | 2 |
| 1 | 8 |
| 2 | 2 |
| Sites of disease[1] | |
| Skin | 12 |
| Liver | 3 |
| Lung | 2 |
| Bone | 6 |
| Nodes | 5 |
| Number of previous chemotherapy schedules | |
| 1 | 3 |
| 2 | 4 |
| 3 or more | 5 |

[1]Some patients more than one site

TABLE 2

A. Gene transfer efficiency (BC1)

| Patient | MetXia-P450 dose | Histological detection of transduced cells (β-galactosidase) | | PCR detection of transduced cells | |
|---|---|---|---|---|---|
| | | Biopsy one | Biopsy two | Biopsy one | Biopsy two |
| 101 | 1× | Positive | Positive | ND | Negative |
| 102 | 1× | Negative | Positive | ND | Positive (0.7) |
| 103 | 10× | Negative | Positive | ND | Negative |
| 104 | 10× | Positive | Positive | ND | Positive (0.87) |
| 105 | 100× | Positive | Negative | Negative | Negative |
| 106 | 100× | Positive | Positive | Positive (0.78) | Positive (NQ) |
| 107 | 100× | Positive | Positive | ND | ND |
| 108 | 100× | Positive | Negative | ND | ND |
| 109 | 10× | Negative | Negative | ND | ND |
| 110 | 10× | Negative | Negative | ND | ND |
| 111 | 100× | Positive | Positive | ND | ND |
| 112 | 100× | Positive | Positive | ND | ND |

TABLE 3

Summary of pre-treatment serum CEA and CA15-3, immunohistochemical staining of CEA and h5T4 expression by tumour cells and h5T4 and CEA antibody titres in patients completing at least 8 weeks of treatment (BC1)

| | | | | | | Antibody titres (weeks post injection) | | | | | | | |
|---|---|---|---|---|---|---|---|---|---|---|---|---|---|
| | Clinical | Pro-treatment Serum | | Tumour Biopsy | | CEA | | | | h5T4 | | | |
| Patient No. | Response | CA15-3 | CEA | CEA | h5T4 | 0 | 3 | 8 | 12 | 0 | 3 | 8 | 12 |
| 101 | SD | + | + | − | + | − | − | − | ++++ | − | − | − | ++++ |
| 104 | PR | + | + | + | + | − | − | ++++ | ++++ | − | ++++ | ++++ | ++++ |

TABLE 3-continued

Summary of pre-treatment serum CEA and CA15-3, immunohistochemical staining of CEA and h5T4 expression by tumour cells and h5T4 and CEA antibody titres in patients completing at least 8 weeks of treatment (BC1)

| Patient No. | Clinical Response | Pre-treatment Serum CA15-3 | Pre-treatment Serum CEA | Tumour Biopsy CEA | Tumour Biopsy h5T4 | CEA 0 | CEA 3 | CEA 8 | CEA 12 | h5T4 0 | h5T4 3 | h5T4 8 | h5T4 12 |
|---|---|---|---|---|---|---|---|---|---|---|---|---|---|
| 105 | PD | + | − | − | − | − | + | + | NA | − | ++ | − | NA |
| 107 | SD | + | − | − | + | − | ++ | − | − | − | − | − | − |
| 111 | SD | + | + | + | + | − | − | − | + | + | − | − | − |
| 112 | SD | + | − | + | − | − | − | − | − | − | − | − | − |

Key:
Clinical response: SD = stable disease, PR = partial response, PD = progressive disease
Serum marker: + = elevated at baseline (CEA > 10 ng/ml or CA15-3 > 25 U/ml), − = within normal range
Tumour biopsy: + = positive staining, − = negative stainin.
B. Antibody titres: − = negative, + = titre > 1:20, ++ = titre > 1:40, +++ = titre > 1:80, ++++ = titre > 1:160, NA = not available

TABLE 4

BC2 patient details.

| Patient No. | Dosage Group | D.O.B. | Time on Trial (Weeks) | Lesions Injected | Primary Diagnosis | Comments |
|---|---|---|---|---|---|---|
| BC2-101 | 10× | 25.06.46 | 9 | 2 | Infiltrating Ductal Carcinoma with Liver mets | Trial monitoring complete |
| BC2-102 | 10× | 06.05.38 | 9 | 2 | Breast Adenocarcinoma lung + lymph node mets | Trial monitoring complete |
| BC2-103 | 10× | 29.01.30 | 3 | 2 | Breast Carcinoma | Withdrawn |
| BC2-104 | 10× | 07.08.29 | 9 | 2 | Breast Carcinoma | Trial monitoring complete |
| BC2-201 | 100× | 15.10.64 | 3 | 4 | Breast Carcinoma | Withdrawn |
| BC2-202/222 | 100× | 11.04.28 | 9 + 1 | 1 | Transitional cell carcinoma of the ureter | Trial monitoring complete |
| BC2-203 | 100× | 11.09.53 | 9 | 4 | Breast cancer | Trial monitoring complete |
| BC2-204 | 100× | 02.09.34 | 9 | 2 | Metastatic breast cancer | Trial monitoring complete |

TABLE 5a

5T4 Protein

Timepoint (weeks post-MetXia administration)

| Patient | 0 | 3 | 7 | 9 |
|---|---|---|---|---|
| BC2-101 | 0.5 | | | 1.4 |
| BC2-102 | 0.5 | | | |
| BC2-103 | | 0.8 | n/a | n/a |
| BC2-104 | 1.3 | 1.7 | | 1.4 |
| BC2-201 | | | n/a | n/a |
| BC2-202 | | | | |
| BC2-203 | 1.5 | 0.7 | | 1.2 |
| BC2-204 | 1.6 | | 1.8 | 1.5 |
| BC2-222 | | n/a | n/a | n/a |

TABLE 5b

5T4 Peptides

Timepoint (weeks post-MetXia administration)

| Patient | Peptide | 0 | 3 | 7 | 9 |
|---|---|---|---|---|---|
| BC2-101 | Pep #41 | 1.4 | 1.1 | | 1.5 |
| BC2-102 | Pep #41 | 0.6 | | | |
| BC2-103 | Pep #41 | 1.5 | | n/a | n/a |
| BC2-104 | Pep #44 | 0.4 | 1.2 | | |
| BC2-201 | Pep #40 | | | n/a | n/a |
| BC2-202 | Pep #40 | | 0.7 | | |
| BC2-203 | Pep #41 | | 0.7 | 0.6 | 0.4 |
| BC2-204 | Pep #41 | 0.7 | 0.5 | 1.2 | 0.5 |
| BC2-222* | Pep #40 | | n/a | n/a | n/a |

TABLE 5c

CEA

Timepoint (weeks post-MetXia administration)

| Patient | 0 | 3 | 7 | 9 |
|---|---|---|---|---|
| BC2-101 | | | | |
| BC2-102 | | | | |
| BC2-103 | | | n/a | n/a |
| BC2-104 | | | 0.4 | 0.5 |
| BC2-201 | | | n/a | n/a |
| BC2-202 | 1.6 | 1 | 1.6 | |
| BC2-203 | | 0.5 | 0.3 | 0.1 |
| BC2-204 | 0.5 | 0.5 | 1.1 | 0.2 |
| BC2-222* | 0.6 | n/a | n/a | n/a |

*Patient 222 is patient 202 who re-entered the trial after completing the 9 week follow-up period to have an additional lesion treated.

TABLE 6

Tumour antigen profiling in biopsies taken from BC2 patients. The table details the distribution of positive cells within the biopsy.

| | Tumour Antigen | | | | |
|---|---|---|---|---|---|
| Patient | Muc-1 | Her-2/neu | Survivin | CEA | 5T4 |
| BC2-101 | ++ c | +++ c, m | − | +++ c | ++ |
| BC2-102 | ++ c | ++ c | + c | +++ c | ++ |
| BC2-103 | ++ | + | − | + | − |
| BC2-104 | ++ | ++ | − | + | − |
| BC2-201 | ++ | ++ | − | + | − |
| BC2-202 | − | − | − | − | − |
| BC2-203 | +/− | − | − | +/− | − |
| BC2-204 | ++++ c, m | ++++ c, m | +/− | ++++ c, m | + c |

Key:
s = stromal, c = cytoplasmic, m = membranous, N/A = Not Available
− No Staining
+ 1-10% cells positive
++ 11-25% cells positive
+++ 26-50% cells positive
++++ 51-100% cells positive

TABLE 7

| | Proliferative Responses | | | TAA Staining | |
|---|---|---|---|---|---|
| Patient | 5T4 Prot | 5T4 Pep | CEA | 5T4 | CEA |
| BC2-101 | Yes | Yes | No | Yes | Yes |
| BC2-102 | Yes | Yes | Yes | Yes | Yes |
| BC2-103 | No | Yes | No | No | Yes |
| BC2-104 | Yes | Yes | Yes | No | Yes |
| BC2-201 | No | No | No | No | Yes |
| BC2-202 | No | No | Yes | No | No |
| BC2-203 | Yes | No | No | No | Yes |
| BC2-204 | Yes | No | No | Yes | Yes |

All publications mentioned in the above specification, and references cited in said publications, are herein incorporated by reference. Various modifications and variations of the described methods and system of the present invention will be apparent to those skilled in the art without departing from the scope and spirit of the present invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

The invention claimed is:

1. A method for stimulating anti-tumor immune responses in a subject having a 5T4 antigen-expressing tumor and a Carcinoembryonic antigen (CEA)-expressing tumor, comprising administering a 5T4 antigen to the subject, wherein the 5T4 antigen stimulates a first anti-tumor immune response directed against the 5T4 antigen-expressing tumor in the subject, and stimulates a second anti- tumor immune response directed against the CEA-expressing tumor in the subject.

2. The method according to claim 1, wherein the immune response directed against a 5T4 antigen-expressing tumor is a T-cell response, an antibody response, or a combined T-cell and antibody response.

3. The method according to claim 1, wherein administering a 5T4 antigen to the subject comprises administering a polynucleotide sequence that encodes the 5T4 antigen to the subject.

4. The method according to claim 1, wherein the immune response directed against the CEA-expressing tumor is a T-cell response, an antibody response, or a combined T-cell and antibody response.

5. The method according to claim 3, wherein administering a polynucleotide sequence that encodes the 5T4 antigen to the subject comprises administering a virus vector that encodes the 5T4 antigen to the subject.

6. The method of claim 5, wherein the virus vector is a vaccinia virus vector.

7. The method of claim 1, wherein the subject is human.

8. The method according to claim 1, further comprising identifying a subject having a tumor that expresses CEA prior to administering a 5T4 antigen to the subject.

9. A method for stimulating an anti-tumor immune response directed against Carcinoembryonic antigen (CEA) in a subject having a CEA-expressing tumor and a 5T4 expressing tumor, comprising administering a 5T4 antigen to the subject, wherein the 5T4 antigen stimulates a first anti-tumor immune response directed against the tumor that expresses 5T4 antigen in the subject and a second anti-tumor immune response directed against the tumor that expresses Carcinoembryonic antigen (CEA) in the subject.

10. The method according to claim 9, wherein the first anti-tumor immune response is a T-cell response, an antibody response, or a combined T-cell and antibody response.

11. The method according to claim 9, wherein the second anti-tumor immune response is a T-cell response, an antibody response, or a combined T-cell and antibody response.

12. The method according to claim 9, wherein administering a 5T4 antigen to the subject comprises administering a polynucleotide sequence that encodes the 5T4 antigen to the subject.

13. The method according to claim 12, wherein administering a polynucleotide sequence that encodes the 5T4 antigen to the subject comprises administering a virus vector that encodes the 5T4 antigen to the subject.

14. The method of claim 13, wherein the virus vector is a vaccinia virus vector.

15. The method of claim 9, wherein the subject is human.

16. The method according to claim 9, further comprising identifying a subject having a tumor that expresses CEA prior to administering a 5T4 antigen to the subject.

* * * * *